United States Patent [19]

Boeck et al.

[11] Patent Number: 4,994,270
[45] Date of Patent: Feb. 19, 1991

[54] A54145 ANTIBIOTICS AND PROCESS FOR THEIR PRODUCTION

[75] Inventors: LaVerne D. Boeck, Indianapolis; David S. Fukuda, Brownsburg; Jon S. Mynderse, Indianapolis; Marvin M. Hoehn, Indianapolis; Ralph E. Kastner, Indianapolis; Harold R. Papiska, Indianapolis, all of Ind.

[73] Assignee: Eli Lilly and Company, Indianapolis, Ind.

[21] Appl. No.: 179,773

[22] Filed: Apr. 11, 1988

[51] Int. Cl.$^5$ ................ A61K 35/74; C07K 7/54
[52] U.S. Cl. ............................. 424/118; 514/9; 514/11; 530/317; 530/323; 426/635; 435/71.3; 435/8.96; 435/169
[58] Field of Search .............. 530/317, 323; 435/69, 435/169, 71, 896; 514/9, 11; 426/635; 424/118

[56] References Cited

U.S. PATENT DOCUMENTS

| Re. 31,396 | 9/1983 | Hamill et al. | 260/112.5 R |
|---|---|---|---|
| Re. 32,333 | 1/1987 | Hamill et al. | 530/321 |
| Re. 32,455 | 7/1987 | Hamill et al. | 530/317 |
| 4,024,245 | 5/1977 | Hoehm et al. | 435/68 |
| 4,208,403 | 6/1980 | Hamill et al. | 424/115 |
| 4,331,594 | 5/1982 | Hamill et al. | 530/317 |
| 4,638,047 | 1/1987 | Szelke et al. | 530/332 |

OTHER PUBLICATIONS

J. Normansell, *The Bacteria*, vol. IX, Chapter 4, "Isolation of Streptomyces Mutants Improved for Antibiotic Production", pp. 95–119, 1986.

A. Fantini, *Methods in Enzymology*, vol. XLIII, "Methods for the Study of Antibiotics, Strain Development," pp. 24–41, 1975.

S. Queener and D. Lively, *The Manual of Industrial Microbiology and Biotechnology*, Chapter 12, "Screening and Selection for Strain Improvement," pp. 155–169, 1986.

*Primary Examiner*—Johnnie R. Brown
*Assistant Examiner*—Christina Chan
*Attorney, Agent, or Firm*—Joseph A. Jones; Leroy Whitaker; Nancy J. Harrison

[57] ABSTRACT

New peptide antibiotic A54145, individual A54145 components A, $A_1$, B, $B_1$, C, D, E and F and their pharmaceutically acceptable salts, are useful antibacterial agents which also improve growth performance in animals, especially poultry. Biologically pure cultures of the A54145-producing *Streptomyces fradiae* cultures NRRL 18158, NRRL 18159 and NRRL 18160 cultures and methods of making antibiotic A54145 using those cultures are also provided.

25 Claims, 9 Drawing Sheets

4,994,270

A54145 ANTIBIOTICS AND PROCESS FOR THEIR PRODUCTION

SUMMARY OF THE INVENTION

This invention relates to a new lipopeptide antibiotic, designated antibiotic A54145, its individual components, designated A, B, C, D, E, F, $A_1$ and $B_1$, and their salts (the A54145 antibiotics).

The A54145 antibiotics inhibit the growth of pathogenic organisms, especially Gram-positive bacteria, and improve growth performance in animals such as poultry. Thus, antibacterial compositions, growthpromoting compositions and methods for using these compositions are also part of this invention.

The invention further relates to three new strains of Streptomyces fradiae, NRRL 18158, NRRL 18159 and NRRL 18160, which produce the A54145 antibiotics and to processes for producing the A54145 antibiotics which comprise culturing an S. fradiae strain selected from NRRL 18158, NRRL 18159 and NRRL 18160 under submerged aerobic fermentation conditions until the antibiotics are produced.

DESCRIPTION OF THE DRAWINGS

The $^1$H NMR spectra of the following A54145 antibiotics (in $D_2O$) are presented in the accompanying drawings.

DETAILED DESCRIPTION OF THE INVENTION

Background of the Invention

Figure 1:
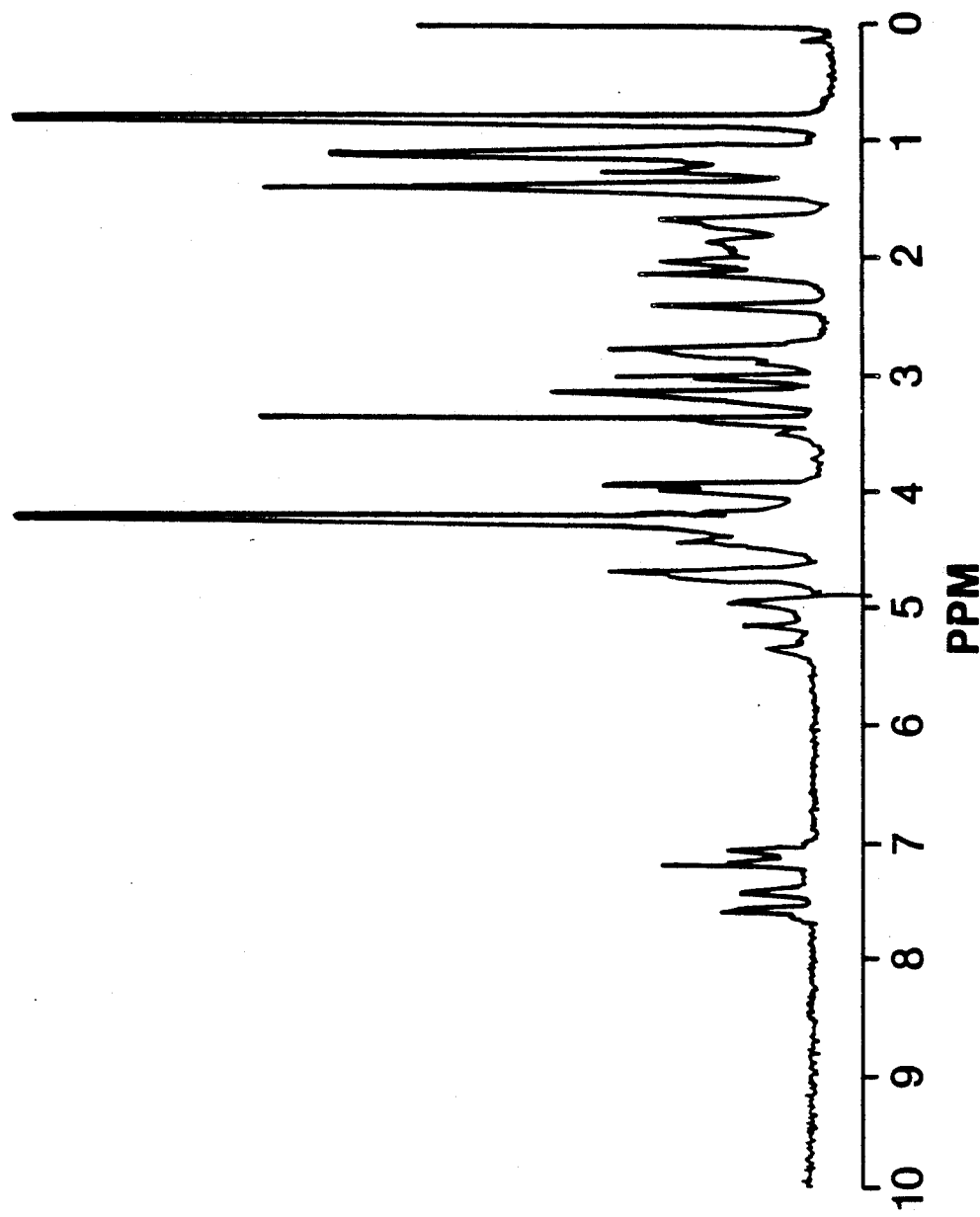
FIG. 1—A54145A
FIG. 2—A54145B
FIG. 3—A54145C
FIG. 4—A54145D
FIG. 5—A54145E
FIG. 6—A54145F
FIG. 7—A54145$A_1$
FIG. 8—A54145$B_1$

Although many antibacterial agents are known, the need for improved antibacterial agents continues. One reason for this need is that antibiotics differ in their effectiveness against a large variety of pathogenic organisms. A second reason is that, unfortunately, organism strains which are resistant to currently used antibiotics continually develop. Yet another reason is the fact that individual patients often suffer serious reactions to specific antibiotics, due to hypersensitivity and/or to toxic effects. There is, therefore, a continuing need for new and improved antibiotics.

The A54145 antibiotics are acidic lipopeptide antibiotics. Previously recognized members of this class of antibiotics include the A-21978C antibiotics (see U.S. Pat. No. 4,331,594), the A-30912 antibiotics (see U.S. Pat. No. 4,024,245), crystallomycin, amphomycin, zaomycin, aspartocin and glumamycin [see T. Korzybski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., J. Antibiotics 21, 439–443 (1968)]; laspartomycin [H. Naganawa, et al J. Antibiotics 21, 55–62 (1968)]; brevistin [J. Shoji and T. Kato, J. Antibiotics 29, 380–389 (1976)]; cerexin A [J. Shoji, et al., J. Antibiotics 29, 1268–1274 (1976)] and cerexin B [J. Shoji and T. Kato, J. Antibiotics 29, 1275–1280 (1976)].

Antibiotic A54145 of this invention comprises a family of co-produced, closely related lipopeptide antibiotics. As will be recognized by those familiar with antibiotic production by fermentation, the number and ratio of individual components produced will vary, depending upon the fermentation conditions used. When antibiotic A54145 is produced under normal conditions, A54145A and A54145B are the most abundant factors, and A54145B, A54145C, A54,145D, A54145E, A54145F and A54145$A_1$ are present in lesser amounts. As is disclosed in the copending application of LaVerne D. Boeck entitled PROCESSES FOR PREPARING A54145 COMPOUNDS, Ser. No. 07/179,930, filed this same day, certain A54145 components may be produced in higher yields by precursing the A54145 fermentation with specific alkanoic acids and/or esters or by feeding glucose and/or enzymatic soy digest during the production stage of the fermentation.

In discussions of utility, the term "A54145 antibiotic" will be used, for the sake of brevity, to denote a member selected from the group consisting of antibiotic A54145, individual components A54145A, A54145B, A54145C, A54145D, A54145E, A54145F, A54145$A_1$ and A54145$B_1$ and their physiologically acceptable salts.

Antibiotic A54145 is produced by fermentation of a Streptomyces fradiae strain selected from NRRL 18158, NRRL 18159 and NRRL 18160. Antibiotic A54145 can be obtained by filtering the fermentation broth, adjusting the pH of the filtrate to about pH 6, adsorbing the filtrate onto a resin such as HP-20 (Diaion) and eluting the antibiotic with a suitable solvent. Antibiotic A54145 can be further purified and separated into its individual components by known techniques such as adsorption. Individual A54145 components A, $A_1$, B, $B_1$ C, D, E and F have been isolated in this manner.

In discussions herein, the following abbreviations will be used:

| Abbreviation | Term |
| --- | --- |
| Ala: | Alanine |
| Asn: | Asparagine |
| (OH)Asn: | β-Hydroxy-asparagine |
| Asp: | Aspartic acid |
| (MeO)Asp: | β-Methoxy-aspartic acid |
| Glu: | Glutamic acid |
| Gly: | Glycine |
| Ile: | Isoleucine |
| Lys: | Lysine |
| Thr: | Threonine |
| Trp: | Tryptophan |
| Sar: | Sarcosine |
| Val: | Valine |
| 3-MG: | 3-Methylglutamic acid |
| HPLC: | High performance liquid chromatography |
| $^1$H NMR: | Proton nuclear magnetic resonance |
| TLC: | Thin-layer chromatography |
| IR: | Infrared |
| UV: | Ultraviolet |
| FABMS: | Fast-atom-bombardment mass spectrometry |

The abbreviation "R-TRP" is used to designate a group of the following structure

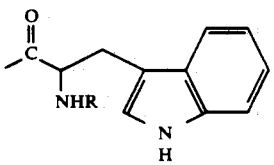

where R is 8-methylnonanoyl, n-decanoyl, or 8-methyldecanoyl.

A54145A, A54145D and A54145A₁ have a common cyclic peptide which is designated the "A nucleus". A54145B, A54145B₁ and A54145E also have a common nucleus which is called the "B nucleus". A54145C and A54145F have unique cyclic peptide nuclei which are called "C nucleus" and "F nucleus", respectively.

Table I summarizes the molecular weights, nucleus types and side-chain lengths of the A54145 antibiotics.

TABLE I

| Comparison of the A54145 Antibiotics | | | |
|---|---|---|---|
| Component | Mol. Wt. | Nucleus | Acyl Group[a] |
| A | 1643 | A | i-$C_{10}$ |
| B | 1657 | B | n-$C_{10}$ |
| C | 1657 | C | a-$C_{11}$ |
| D | 1657 | A | a-$C_{11}$ |
| E | 1671 | B | a-$C_{11}$ |
| F | 1629 | F | i-$C_{10}$ |
| $A_1$ | 1643 | A | n-$C_{10}$ |
| $B_1$ | 1657 | B | i-$C_{10}$ |

[a] i-$C_{10}$ = 8-methylnonanoyl
n-$C_{10}$ = n-decanoyl
a-$C_{11}$ = 8-methyldecanoyl The four A54145 cyclic peptides (the A, B, C and F nuclei) have been obtained and are described in the copending application of David S. Fukuda and Jon S. Mynderse entitled A54145 CYCLIC PEPTIDES, Ser. No. 07/179,928, filed herewith this same day. Amino-acid sequencing of the A and B nuclei and fast-atom-bombardment mass spectrometry (FABMS) of the antibiotics/nuclei suggest the common structure 1 and individual structures 1a–1d for the A54145 nuclei:

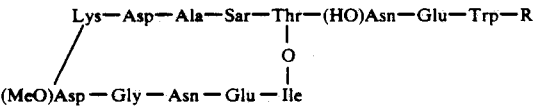

| Structure | A54145 Nucleus | X | Y |
|---|---|---|---|
| 1a | A | Ile | Glu |
| 1b | B | Ile | 3-MG |
| 1c | C | Val | 3-MG |
| 1d | F | Val | Glu |

Thus, the A54145 antibiotics are believed to have general structure 2 and specific structures 2a–2h:

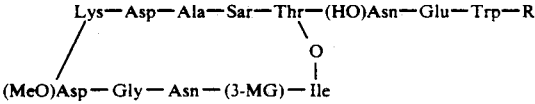

| Structure | A54145 | X | Y | R |
|---|---|---|---|---|
| 2a | A | Ile | Glu | 8-methylnonanoyl |
| 2b | B | Ile | 3-MG | n-decanoyl |
| 2c | C | Val | 3-MG | 8-methyldecanoyl |
| 2d | D | Ile | Glu | " |
| 2e | E | Ile | 3-MG | " |

-continued

| Structure | A54145 | X | Y | R |
|---|---|---|---|---|
| 2f | F | Val | Glu | 8-methylnonanoyl |
| 2g | $A_1$ | Ile | Glu | n-decanoyl |
| 2h | $B_1$ | Ile | 3-MG | 8-methylnonanoyl |

The individual A54145 components have the following characteristics:

A54145A

Mol. Wt.: 1643

Mol. Formula: $C_{72}H_{109}N_{17}O_{27}$

High Resolution FABMS(M+H): Found: 1644.7778, Calcd. for $C_{72}H_{110}N_{17}O_{27}$: 1644.7757

UV (EtOH) $\lambda_{max}$: 219 nm ($\epsilon$ 35,000), 280 ($\epsilon$ 5,250), shoulder 288 ($\epsilon$ 4,600)

IR (KBr): essentially the same as that of A54145B, infra.

Optical Rotation $[\alpha]_{589}^{25°\ C.}$ No Rotation (CH₃OH); $[\alpha]_{365}^{25°\ C.} = -14.0°$ (c 1.0, CH₃OH)

Amino-acid Analysis Asp 973(2), Thr 441(1), Glu 1056(2), Gly 528(1), Ala 549(1), Ile 469(1), Trp 465(1)

¹H NMR (360 MHz): see FIG. 1

Tentative Structure

```
         Lys—Asp—Ala—Sar—Thr—(HO)Asn—Glu—Trp—R
        /                                      \
       /                                        O
      /                                         |
(MeO)Asp—Gly—Asn—Glu—Ile
``` where R is 8-methylnonanoyl.

A54145B

Mol. Wt.: 1657

Mol. Formula: $C_{73}H_{111}N_{17}O_{27}$

High Resolution FABMS(M+H): Found: 1658.7954, Calcd. for $C_{73}H_{112}N_{17}O_{27}$: 1658.7914

UV (EtOH) $\lambda_{max}$: 220 nm ($\epsilon$41,854), 281 ($\epsilon$ 5,613), 289 ($\epsilon$5,084)

Figure 9:
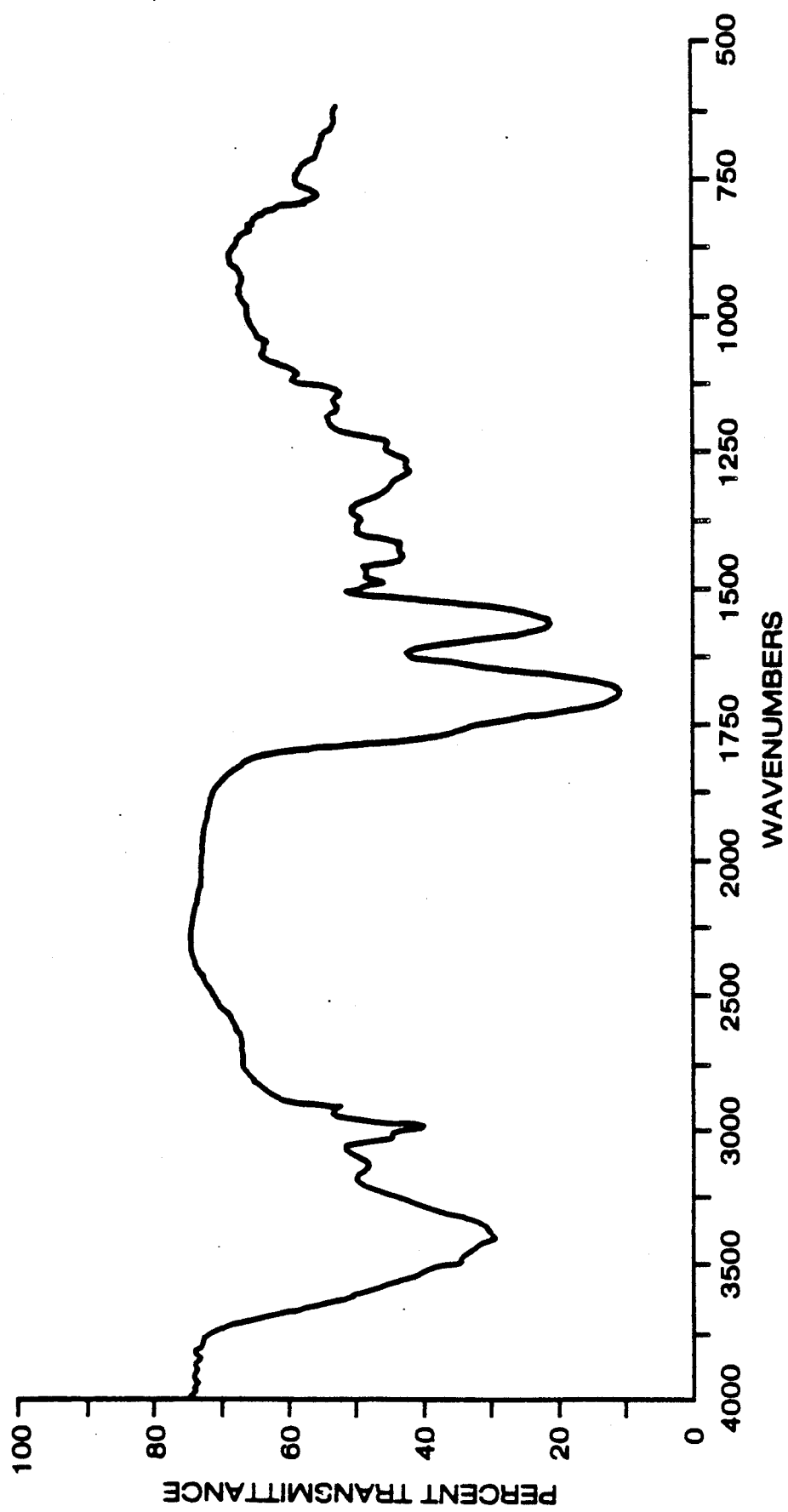
FIG. 9 is the IR spectrum of A54145B in KBr. The IR spectra of the other A54145 components are essentially the same as that of A54145B.

IR (KBr): ranging from 3335 to 3313; 2930, 1660, 1531, 1407, 1255 cm⁻¹ (FIG. 9)

Optical Rotation $[\alpha]_{589}^{25°\ C.} = -8.55°$ (c 0.47, H₂O); $[\alpha]_{365}^{25°\ C.} = -36.32°$ (c 0.47, H₂O)

Amino-acid Analysis: Asp 1039(2), Thr 466(1), Glu 564(1), Gly 528(1), Ala 525(1), Ile 491(1), Lys 514(1), Trp 491(1), 3-MG 512(1).

Figure 2:
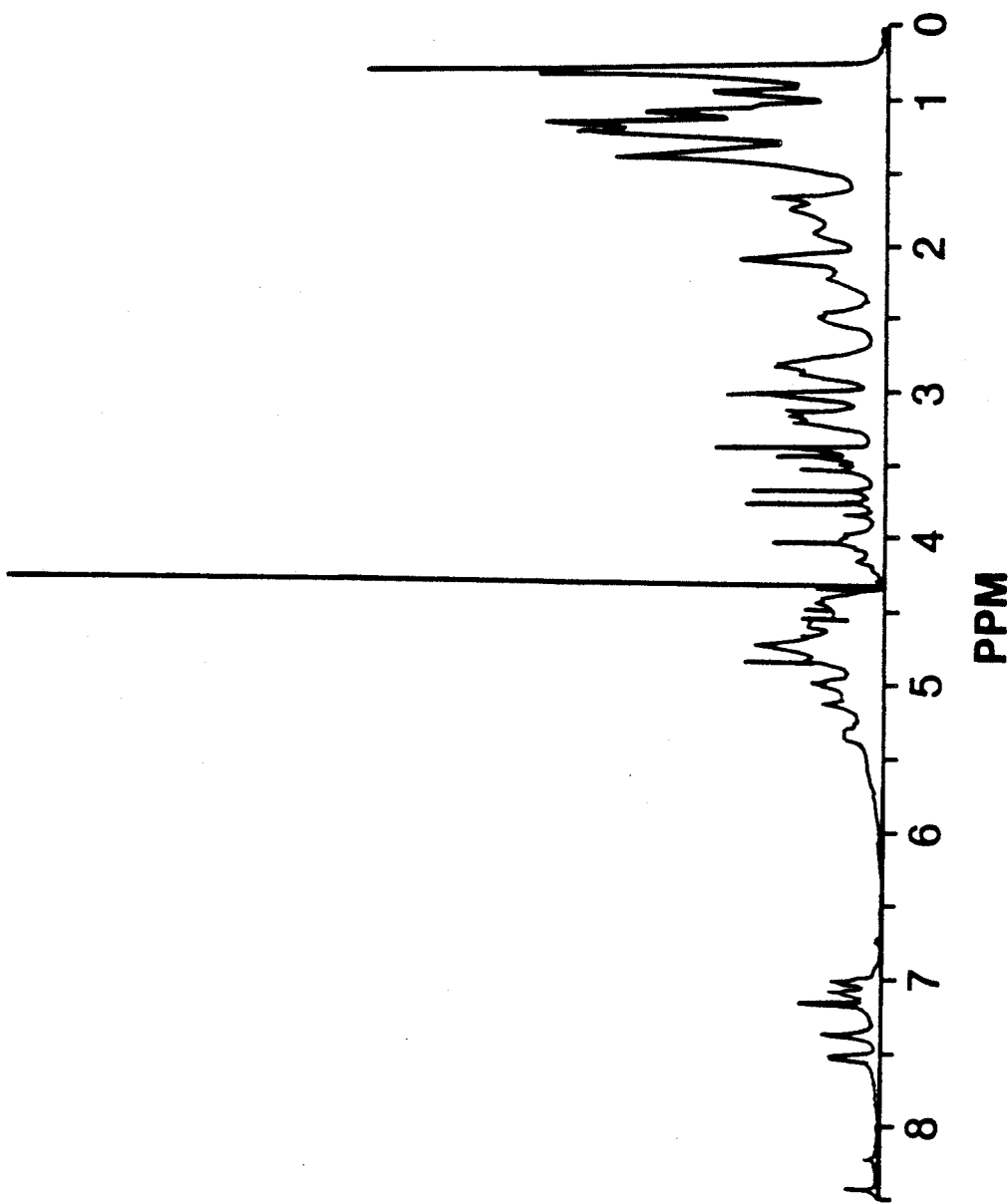

¹H NMR (360 MHz): see FIG. 2

Tentative Structure:

```
         Lys—Asp—Ala—Sar—Thr—(HO)Asn—Glu—Trp—R
        /                                      \
       /                                        O
      /                                         |
(MeO)Asp—Gly—Asn—(3-MG)—Ile
``` where R is n-decanoyl.

A54145C

Mol. Wt.: 1657

Mol. Formula: $C_{73}H_{111}N_{17}O_{27}$;

High Resolution FABMS(M+H): Found: 1658.7905, Calcd. for $C_{73}H_{112}N_{17}O_{27}$: 1658.7914

UV (EtOH) $\lambda_{max}$: 219 nm ($\epsilon$29,500), 281 ($\epsilon$4,200), 288 ($\epsilon$3,600)

IR (KBr): essentially the same as that of A54145B, supra.

Amino-acid Analysis: Asp 934(2), Thr 414(1), Glu 594(1), Gly 501(1), Ala 459(1), Val 359(1), Lys 451(1), 3-MG 487(1), Trp 308(1).

Figure 3:
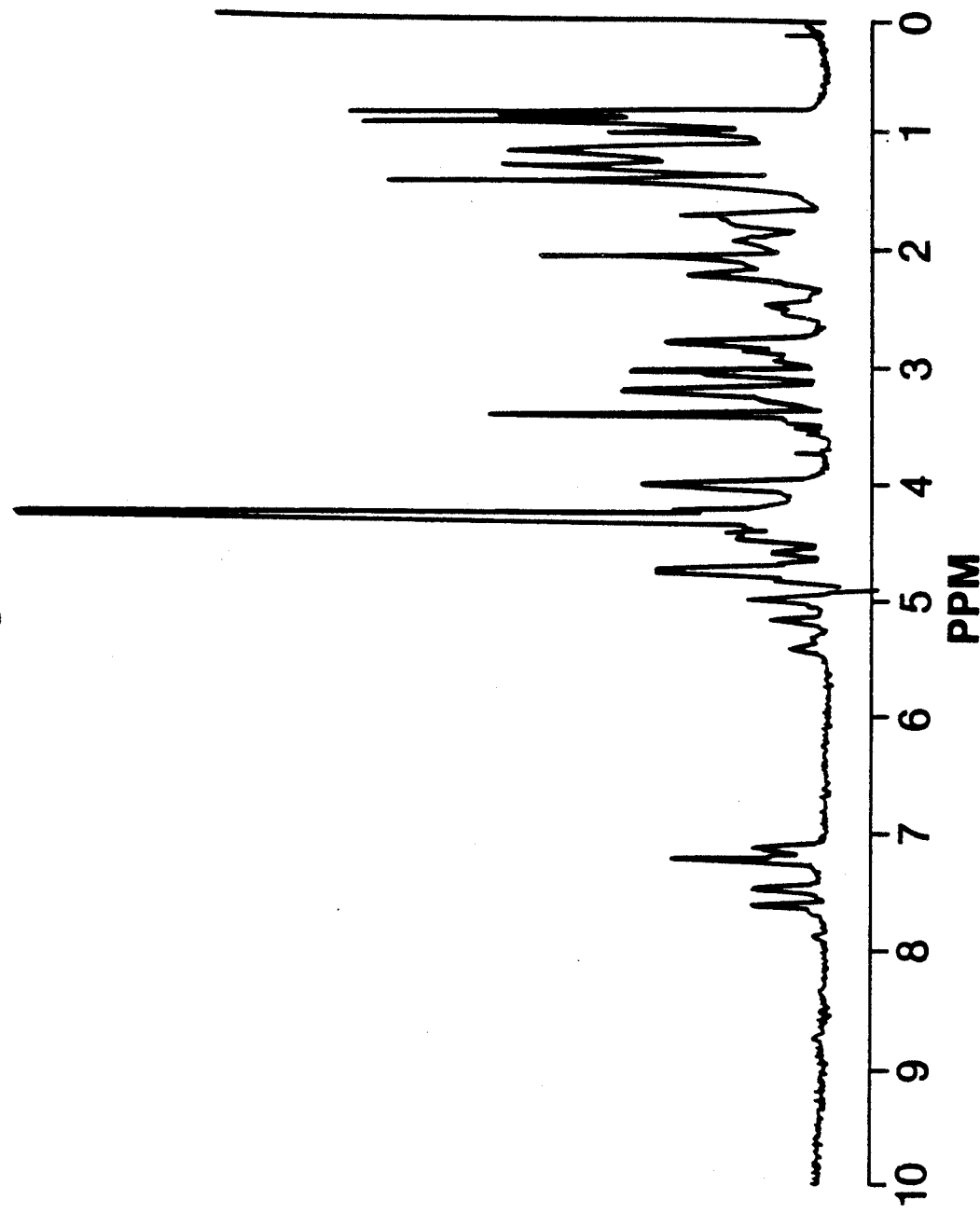

$^1$H NMR (360 MHz): see FIG. 3
Tentative Structure:

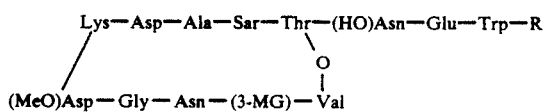

where R is 8-methyldecanoyl.

A54145D

Mol. Wt.: 1657
Mol. Formula: $C_{73}H_{111}N_{17}O_{27}$
High Resolution FABMS(M+H): Found: 1658.7913, Calcd. for $C_{73}H_{112}N_{17}O_{27}$: 1658.7914

UV (EtOH) $\lambda_{max}$: 219 nm ($\epsilon$ 37,500) 280 ($\epsilon$ 5,200), 288 ($\epsilon$ 4,500)

IR (KBr): essentially the same as that of A54145B, supra.

Amino-acid Analysis Asp 1011(2), Thr 427(1), Glu 967(2), Gly 515(1), Ala 487(1), Ile 434(1), Lys 543(1), Trp 577(1)

Figure 4:
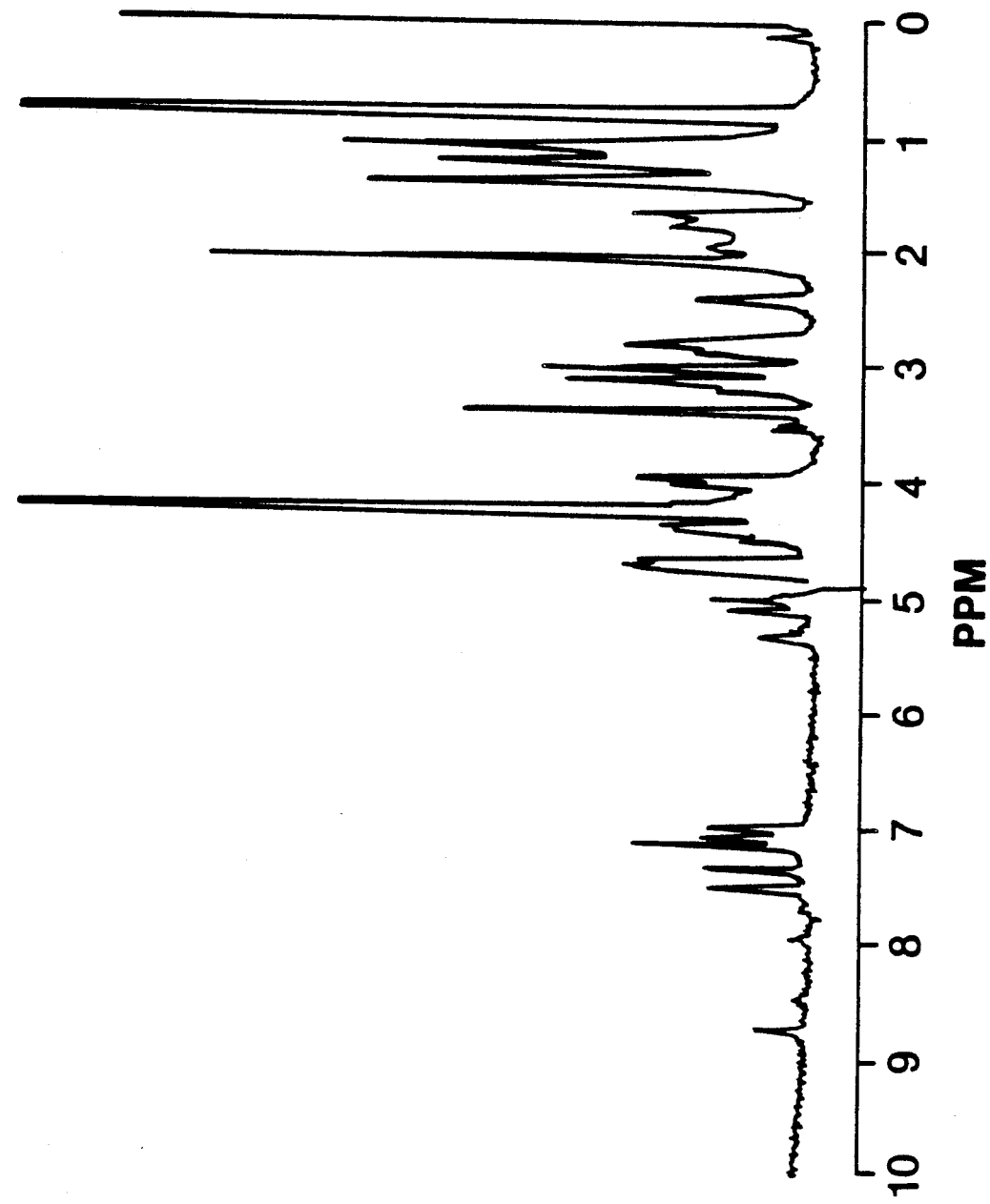

$^1$H NMR (270 MHz): see FIG. 4.
Tentative Structure:

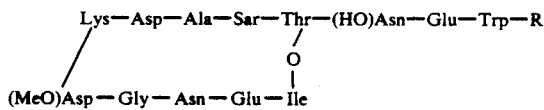

where R is 8methyldecaonyl.

A54145E

Mol. Wt.: 1671
Mol. Formula: $C_{74}H_{113}N_{17}O_{27}$
High Resolution FABMS(M+H): Found: 1672.8065, Calcd. for $C_{74}H_{114}N_{17}O_{27}$: 1672.8069

UV (EtOH) $\lambda_{max}$: 221 nm ($\epsilon$ 29,714), 278 ($\epsilon$ 4,577), 289 (4,044)

IR (KBr): essentially the same as that of A54145B, supra.

Amino-acid Analysis: Asp 826(2), Thr 367(1), Glu 494(1), Gly 437(1), Ala 422(1), Ile 378(1), Lys 410 (1), Trp 387(1), 3-MG 437(1)

Figure 5:
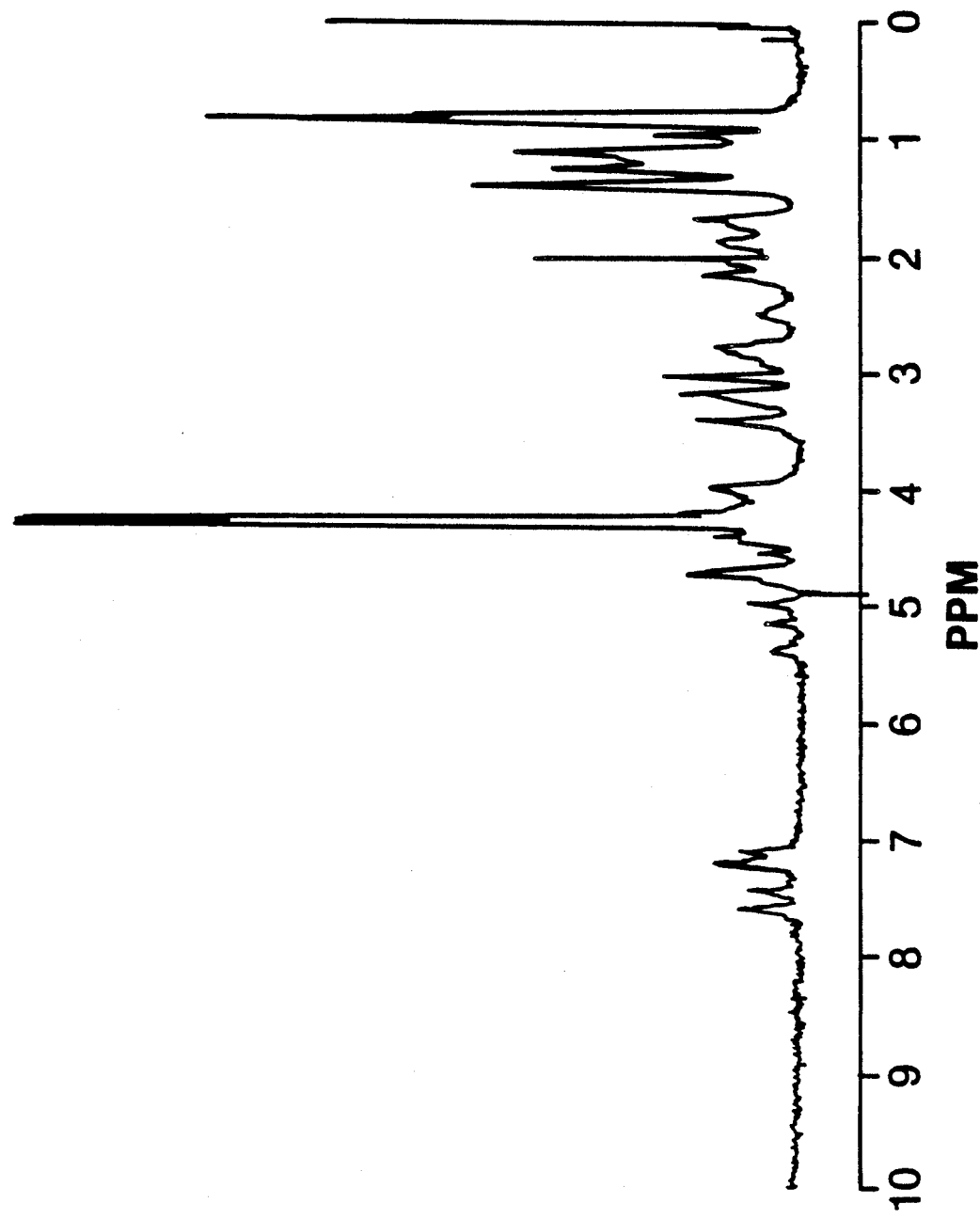

$^1$H NMR (270 MHz): see FIG. 5
Tentative Structure:

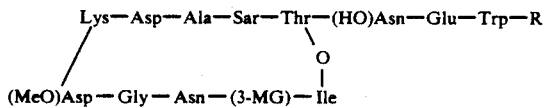

where R is 8-methyldecanoyl.

A54145F

Mol. Wt.: 1629
Mol. Formula: $C_{71}H_{107}N_{17}O_{27}$
High Resolution FABMS(M+H): Found: 1630.7634 Calcd for $C_{71}H_{108}N_{17}O_{27}$: 1630.7601

UV (EtOH) $\lambda_{max}$: 219 nm ($\epsilon$ 36,750), 280 ($\epsilon$, 5,100), 288 ($\epsilon$ 4,450)

IR (KBr): essentially the same as that of A54145B, supra.

Optical Rotation: $[\alpha]_{589}^{25°}$ $^{C.}= -3.0°$ (c 1.0, H$_2$O); $[\alpha]_{365}^{25°}$ $^{C.}= -6.0°$ (c 1.0, H$_2$O)

Amino-acid Analysis: Asp 959(2), Thr 428(1), Glu 965(2), Gly 494(1), Ala 487(1), Val 363(1), Lys (1), Trp 452(1).

Figure 6:
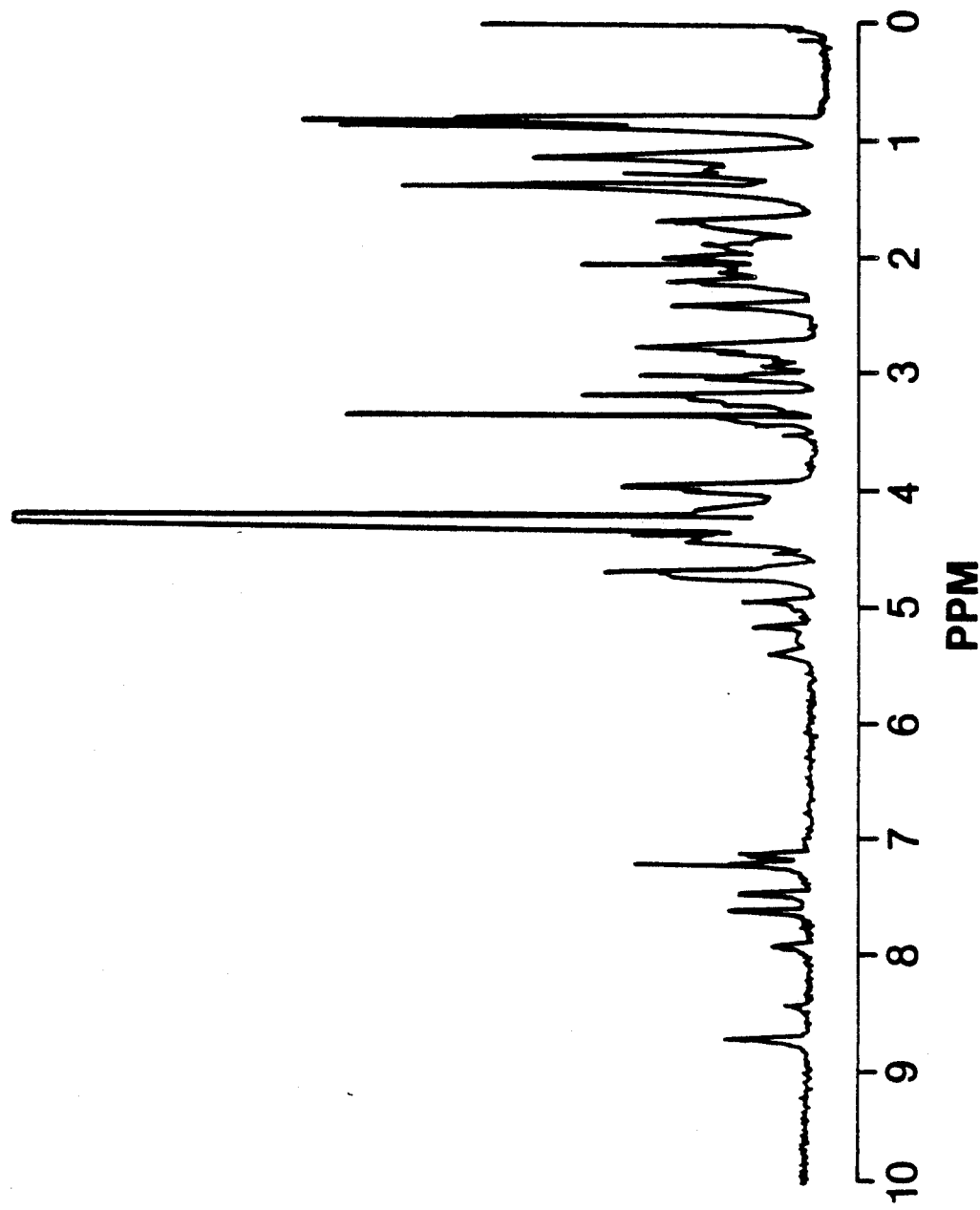

$^1$H NMR (270 MHz): see FIG. 6
Tentative Structure:

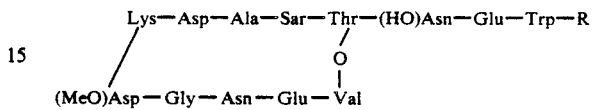

where R is 8-methylnonanoyl.

A54145A$_1$

Mol. Wt.: 1643
Mol. Formula: $C_{72}H_{109}N_{17}O_{27}$
High Resolution FABMS(M+H): Found: 1644.7691, Calcd for $C_{72}H_{110}N_{17}O_{27}$: 1644.7757

UV (EtOH) $\lambda_{max}$: 220 nm ($\epsilon$ 41,623), 281 ($\epsilon$, 5,750), 289 ($\epsilon$ 4,950)

IR(KBr): essentially the same as that of A54145B, supra.

Optical Rotation: $[\alpha]_{589}^{25°}$ $^{C.}-10.4°$ (c 0.69, CH$_3$OH)

Amino-acid Analysis: Asp 1209(2), Thr 554(1), Glu 1209(2), Gly 636(1), Ala 617(1), Ile 576(1), Lys 604(1), Trp 514(1)

Figure 7:
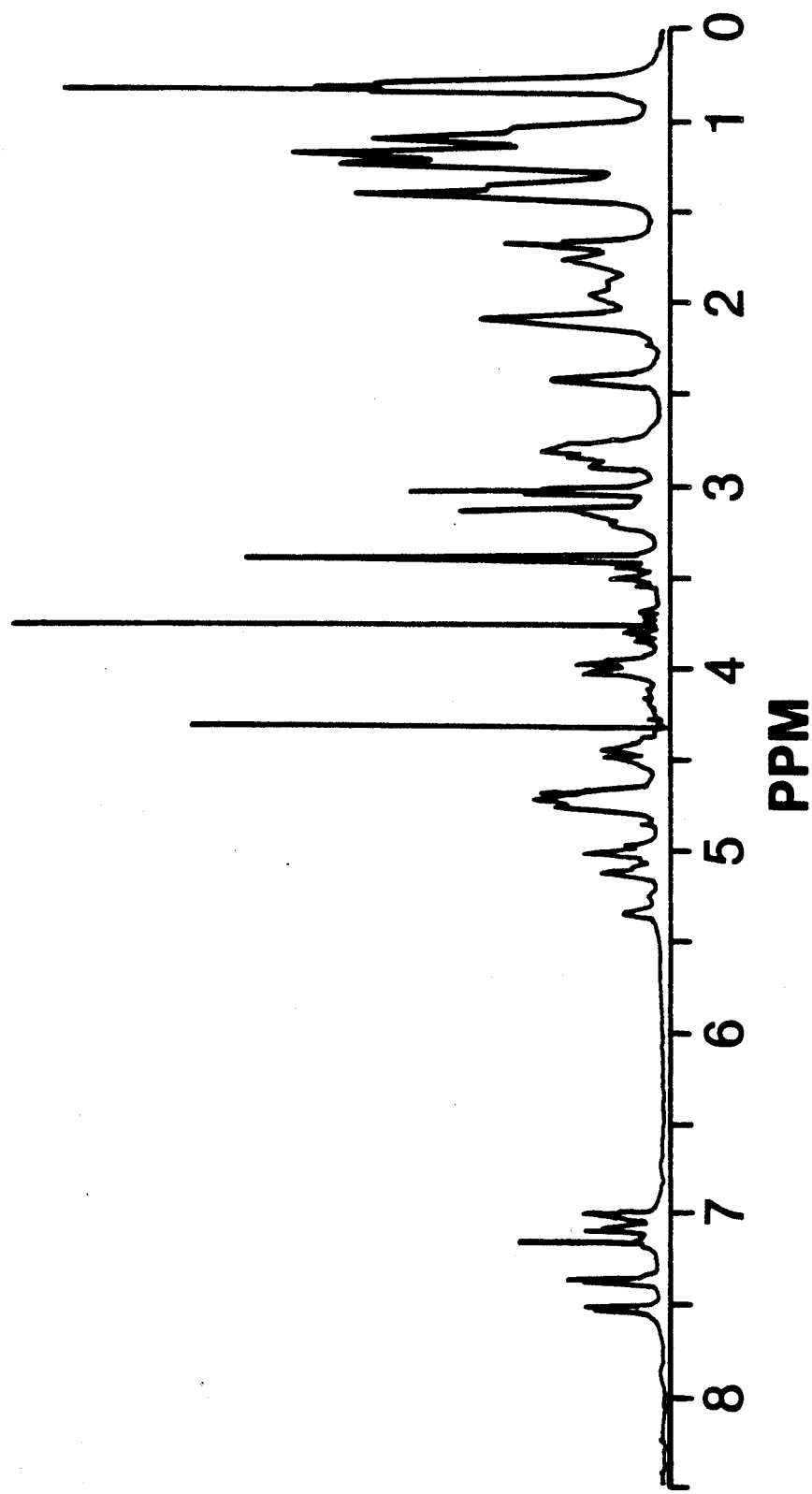

$^1$H NMR (5000 MHz): see FIG. 7
Tentative Structure:

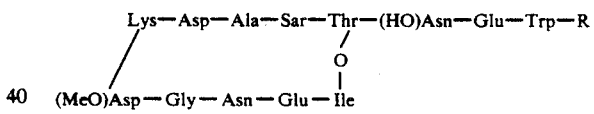

where R is n-decanoyl.

A54145B$_1$

Mol. Wt.: 1657
Mol. Formula: $C_{73}H_{111}N_{17}O_{27}$
High Resolution FABMS(M+H): Found: 1658.7911 Calcd. for $C_{73}H_{112}N_{17}O_{27}$: 1658.7914

UV (EtOH) $\lambda_{max}$: 221 nm ($\epsilon$ 39,100), 282 ($\epsilon$ 5,500), 290 ($\epsilon$ 4,740)

IR (KBr): essentially the same as that of A54145B, supra.

Amino-acid Analysis: Asp 935(2), Thr 422(1), Glu 556(1), Gly 480(1), Ala 434(1), Ile 438(1), Lys 467(1), Trp 440(1), 3-MG 426(1);

Tentative Structure:
$^1$H NMR (500 MHz): see FIG. 8

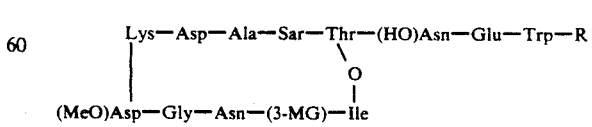

where R is 8-methylnonanoyl.

Antibiotic A54145 and its individual components (as Na salts) are soluble in water and in acidic and alkaline solutions, except at pH levels of below about pH 3.5; in lower alcohols such as methanol and ethanol; and in dimethylformamide and dimethyl sulfoxide; but are only slightly soluble or are insoluble in acetone, chloroform, diethyl ether, benzene, ethyl acetate, and hydrocarbon solvents. The salt forms of antibiotic A54145 and its components are soluble in water, methanol, dimethylformamide, and dimethyl sulfoxide; but are insoluble in solvents such as ethanol.

Antibiotic A54145 and its individual components A, B, C, D, E, F, $A_1$ and $B_1$ have both carboxyl and amino groups which can form salts, such as alkali-metal, alkaline-earth-metal, amine and acid-addition salts. Partial, mixed and complete salts are, therefore, contemplated as part of this invention. Such salts are useful, for example, for separating and purifying the antibiotic and its components.

Representative alkali-metal and alkaline-earth-metal salts of the A54145 antibiotics include the sodium, potassium, lithium, cesium, rubidium, barium, calcium and magnesium salts.

The alkali-metal and alkaline-earth-metal cationic salts of the A54145 antibiotics are prepared according to procedures commonly used for the preparation of cationic salts. For example, the free acid form of A54145A is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

Suitable amine salts of the A54145 antibiotics include the ammonium and the primary, secondary and tertiary $C_1$-$C_4$-alkylammonium and hydroxy-$C_2$-$C_4$-alkylammonium salts. Illustrative amine salts include those formed by reaction of an A54145 antibiotic with ammonium hydroxide, methylamine, sec-butylamine, isopropylamine, diethylamine, di-isopropylamine, ethanolamine, triethylamine, 3-amino-1-propanol and the like.

The salts formed with organic amines can be prepared using standard procedures.

Representative and suitable acid-addition salts of the A54145 antibiotics include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicyclic, methanesulfonic, benzenesulfonic, sortic, picric, benzoic, cinnamic and like acids.

Pharmaceutically acceptable salts are especially useful. "Pharmaceutically-acceptable" salts are those in which the toxicity of the compound as a whole toward warm-blooded animals is not increased relative to the non-salt form. Pharmaceutically-acceptable alkali-metal, alkaline-earth-metal and amine salts and acid-addition salts are particularly useful.

When treating an animal, it is not ordinarily of great significance whether the free base or a salt of a compound is used. A salt form may, however, be chosen for reasons of economy, convenience or toxicity.

The A54145 antibiotics are produced by an A54145-producing strain selected from one of three *Streptomyces fradiae* cultures, NRRL 18158, NRRL 18159 and NRRL 18160, or an A54145-producing mutant of these cultures. Following their production under submerged aerobic conditions in a suitable culture medium, the A54145 antibiotics can be recovered from the culture medium by various isolation and purification procedures understood in the art.

Cultures of the three A54145-producing organisms have been deposited and made part of the stock culture collection of the Midwest Area Northern Regional Research Center, Agricultural Research Service, U.S. Department of Agriculture, 1815 North University Street, Peoria, Ill. 61604, from which they are available to the public under the accession numbers NRRL 18158, NRRL 18159 and NRRL 18160.

The *Streptomyces fradiae* strain NRRL 18158 is a spontaneous mutant which was biologically purified from a culture isolated from a soil sample from Mexico. For convenience in describing this *S. fradiae* strain, it is called the A54145.1 culture. *S. fradiae* strains NRRL 18159 and NRRL 18160 are induced mutant strains obtained from the A54145.1 culture. For convenience, the NRRL 18159 and NRRL 18160 strains are called the A54145.2 and A54145.3 cultures, respectively.

Taxonomic studies of the A54145.1, A54145.2 and A54145.3 cultures were carried out by Frederick P. Mertz of the Lilly Research Laboratories. Based on these studies, the A54145.1 organism is classified as a strain of *Streptomyces fradiae* (Waksman and Curtis 1916) Waksman and Henrici 1948. This classification is based on direct laboratory comparisons and an examination of published descriptions of this species [E. B. Shirling and D. Gottlieb, "Cooperative Description of Type Strains of *Streptomyces*", *Int. J. Syst. Bacteriol.* 18(2):69–189 (1968); and S. A. Waksman, "The Actinomycetes Vol. II", The Williams and Wilkins Co., Baltimore, 1961].

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)]have been followed along with certain supplementary tests (D. J. Blazevic and G. M. Ederer, "Principles of Biochemical Tests in Diagnostic Microbiology", John Wiley and Sons, Inc., New York, 1975, p. 136).

Carbon utilization was determined on ISP No. 9 basal medium to which filter-sterilized carbon sources were added to equal a final concentration of 1.0 percent. Plates were incubated at 30° C and read after 14 days.

Melanoid pigment production (chromogenicity) was determined with ISP No. 1 (tryptone-yeast extract broth), ISP No. 6 (peptone-yeast extract-iron agar), ISP No. 7 (tyrosine agar) and modified ISP No. 7 which has tyrosine removed.

Starch hydrolysis was determined by testing for the presence of starch with iodine on ISP No. 4 (inorganic salts-starch agar) plates (see Blazevic and Ederer, supra).

Morphology was studied using an optical light microscope. A scanning electron microscope (SEM) was used to study the spore-surface ornamentation.

NaCl tolerance was measured by adding NaCl to ISP No. 2 agar to equal the concentration desired.

ICSS-NBS Centroid Color Charts, standard sample No. 2106 (National Bureau of Standards, 1958, U. S. Department of Commerce, Washington, D.C.) and the Color Harmony Manual (4th ed., Color Standards Department, Container Corporation of America, Chicago, Ill., 1958) were used to assign color names.

The isomer of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates", Appl. Microbiol. 12, 421–423 (1964)]and of Lechevalier [M. P. Lechevalier, "Identification of Aerobic Actinomycetes of Clinical Importance", J. Lab. Clin. Med. 71, 934–944 (1968)].

Resistance to lysozyme was measured by methods recommended by Gordon et al. [R. E. Gordon, D. A. Barnett, J. E. Handerhan and C. H. Pang, "Nocardia coeliaca, Nocardia autotrophica and the Nocardia Strain", Int. J. Syst. Bacteriol. 24(1), 54–63 (1974)].

Resistance to antibiotics was measured by padding antibiotic sensitivity discs onto the surface of seeded ISP No. 2 agar plates.

Phosphatase and urease were determined by methods described by Blazevic and Ederer, supra.

Cultural Characteristics

Cultures A54145.1, A54145.2 and A54145.3 did not produce abundant growth or abundant aerial mycelia in any of the 10 agar media tested. Moderate growth and limited aerial hyphae were produced on several complex and defined agar media. The aerial spore mass color was best represented on oatmeal agar (ISP No. 3) and inorganic salts-starch agar (ISP No. 4) media and was in the red (R) color series. The nearest matching color tab in the Tresner and Backus System [H. D. Tresner and E. J. Backus, "System of Color Wheels for Streptomycete Taxonomy," Appl. Microbiol. 11:335–338 (1956)]was 4 ec, grayish yellowish pink.

The reverse side of the cultures did not have a distinctive pigment. They were yellow-brown. A minor distinction between the strains was the tendency of A54145.3 to produce a darker shade of brown than A54145.1 or A54145.2 on ISP No. 3 and tap water agar.

No soluble pigments were produced, except for a light brown pigment seen in yeast-malt extract agar (ISP No. 2). Table II presents these cultural characteristics.

TABLE NO. II

Cultural Characteristics of A54145.1, A54145.2, A54145.3 and S. fradiae[a]

| | | A54145.1 | A54145.2 | A54145.3 | S. fradiae |
|---|---|---|---|---|---|
| ISP No. 2 | G: | Good | Good | Fair | Abundant |
| | R: | 74.s.yBr | 74.s.yBr | 74.s.yBr | 71.m.OY |
| | Am: | Fair: 3ge l.gy.yBr | Good: 3ge l.gy.yBr | Fair: 3ge l.gy.yBr | Abundant: 2ca p.Y |
| | Sp: | Light-brown | Light-brown | Light-Brown | None |
| ISP No. 3 | G: | Fair | Fair | Poor | Good |
| | R: | 57.1.Br | 57.1 Br | 58.m.Br | 76.l.yBr |
| | Am: | Fair: 4ec gy.yPk. | Good: 4ec gy.yPk. | Poor: 4ec gy.yPk. | Good: 4ec gy.yPk. |
| | Sp: | None | None | None | None |
| ISP No. 4 | G: | Fair | Fair | Fair | Good |
| | R: | 78.d.yBr | 75.deep yBr | 75.deep yBr | 74.s.yBr |
| | Am: | Fair: 4ec gy.yPk. | Fair: 4ec gy.yPk. | Poor: 4ec gy.yPk. | Abundant: 3ca p.OY |
| | Sp: | None | None | None | None |
| ISP No. 5 | G: | Fair | Fair | Fair | Good |
| | R: | 87.m.Y | 87.m.Y | 87.m.Y | 70.1.OY |
| | Am: | Fair 2dc yGy | Poor: 2dc yGy | Poor: 2dc yGy | Good: 2ca pY |
| | Sp: | None | None | None | None |
| ISP No. 7 | G: | Fair | Fair | Fair | Good |
| | R: | 88.d.Y | 88.d.Y | 88.d.Y | 72.d.OY |
| | Am: | Poor | Poor | Poor | Good: 3ca p.OY |
| | Sp: | None | None | None | None |
| Czapeks | G: | Poor | Fair | Poor | Fair |
| | R: | 90.gy.Y | 93.y Gray | 77.m.yBr | 70.1.OY |
| | Am: | Trace | Trace | Trace | Fair: 3ca p.OY |
| | Sp: | None | None | None | None |
| Glucose Asparagine | G: | Poor | Trace | Poor | Fair |
| | R: | 88.d.Y | 88.d.Y | 88.d.Y | 88.d.Y |
| | Am: | None | Trace | None | Poor: b White |
| | Sp: | None | None | None | None |
| Glycerol Glycine | G: | Not grown | Not grown | Not grown | Poor |
| | R: | — | — | — | 87.m.Y |
| | Am: | — | — | — | None |
| | Sp: | — | — | — | None |
| Tomato Paste | G: | Fair | Fair | Fair | Fair |
| | R: | 84.s.Y | 74.s.yBr | 74.s.yBr | 94.1.01.Br |
| | Am: | Fair: 4ec gy.yPk | Fair: 4ec gy.yPk. | Fair: 4ec gy.yPk | Fair: 4ec gy.yPk. |
| | Sp: | None | None | None | None |
| Oatmeal Tap Water Agar | G: | Fair | Fair | Fair | Good |
| | R: | 57.1.Br | 57.1.Br | 58.m.Br | 76.l.yBr |
| | Am: | Fair: 4ec gy.yPk | Fair: 4ec gy.yPk. | Fair: 4ec gy.yPk | Good: 4ec gy.yPk |
| | Sp: | None | None | None | None |

[a]G = growth; R = reverse; Am = aerial mycelia; Sp = soluble pigment

Morphological Characteristics

The mycelia of A54145.1, A54145.2 and A54145.3 were non-fragmenting and monopodially branched. Sporophores were short chains of 10 or more spores arranged in a hooked and looped configuration. No differences were observed between the three strains. They were placed in the Retinaculum-apertum (RA) configuration of Pridham [T. G. Pridham, C. W. Hesseltine, and R. C. Benedict, "A Guide for the Classification of Streptomycetes According to Selected Groups," Appl. Microbiol. 6:52–79 (1957)]. Rectus-flexibilis (RF) morphology was also observed.

The hooks and loops were primitive and incomplete. Morphology on some media, such as glycerolasparagine agar (ISP No. 5) and Czapek's solution, was exclusively (RF) configuration. Morphology on other media such as ISP No. 3, ISP No. 4, and tap water agar clearly showed the (RA) configuration.

Scanning electron micrography was done on the parent strain, A54145.1. Spore shape was oblong. The average spore size was 1.5×1.0 μM. The spore-surface ornamentation was smooth (Sm).

Physiological Characteristics

Table III gives the carbohydrate-utilization pattern of these strains.

TABLE III

Utilization of Carbon Compounds by A54145.1, A54145.2, A54145.3 and *S. fradiae*[a]

| | A54145.1 | A54145.2 | A54145.3 | S. fradiae |
|---|---|---|---|---|
| control | − | − | − | − |
| adonitol | − | − | − | − |
| L-arabinose | + | + | + | + |
| cellobiose | + | + | + | + |
| cellulose | − | − | − | + |
| dextran | − | − | − | − |
| D-fructose | + | − | − | + |
| D-galactose | + | + | + | + |
| D-glucose | + | + | + | + |
| i-inositol | − | − | − | − |
| inulin | − | − | − | − |
| D-lactose | + | − | + | + |
| mannitol | − | − | − | − |
| D-mannose | + | + | + | + |
| D-melezitose | − | − | − | − |
| D-melibiose | − | − | − | − |
| raffinose | − | − | − | − |
| L-rhamnose | − | − | − | − |
| ribose | + | + | + | + |
| salicin | − | − | − | + |
| sucrose | − | − | − | + |
| trehalose | + | + | + | + |
| xylitol | − | − | − | − |
| D-xylose | + | + | + | + |

[a] + = utilized; − = not utilized

A54145.1, A54145.2, and A54145.3 had identical antibiotic-resistance patterns. The strains were resistant to lincomycin at 2 μg and penicillin G at 10 units. The strains were sensitive to bacitracin at 10 units, cephalothin at 30 μg, gentamicin at 10 μg, neomycin at 30 μg, oleandomycin at 15 μg, rifampin at 5 μg, streptomycin at 10 μg, tetracycline at 30 μg, tobramycin at 10 μg and vancomycin at 30 μg.

Table IV shows additional physiological characteristics.

TABLE IV

Comparison of A54145.1, A54145.2, A54145.3 and *S. fradia*[a]

| Characteristic | A54145.1 | A54145.2 | A54145.3 | S. fradiae |
|---|---|---|---|---|
| Aerial spore-mass color | red | red | red | red |
| Carbon source utilized | | | | |
| D-fructose | + | − | − | + |
| D-lactose | + | − | + | + |
| salicin | − | − | − | + |
| sucrose | − | − | − | + |
| Catalase production | + | + | + | + |
| Degradation of: | | | | |
| adenine | + | NG[b] | + | + |
| calcium malate | − | − | − | − |
| casein | + | + | + | + |
| chitin | − | − | − | − |
| DNA | + | + | + | + |
| elastin | + | + | + | + |
| esculin | + | + | − | + |
| hippurate | − | − | − | − |
| hypoxanthine | + | + | + | − |
| keratin | − | − | − | − |
| starch | + | + | + | + |
| tyrosine | − | − | − | − |
| xanthine | − | − | − | − |
| Gelatin liquefaction | + | + | − | + |
| H₂S production | + | + | + | − |
| Melanoid pigments | − | − | − | − |
| Morphology | RA | RA | RA | RA |
| NaCl tolerance (percent) | 6 | 4 | 6 | 7 |
| Nitrate reduction | + | + | − | + |
| Phosphatase production | + | + | + | + |
| Resistance to lysozyme | − | − | − | − |
| Reverse side color | Y-Br | Y-Br | Y-Br | Y-Br |
| Skim-milk hydrolysis | − | − | − | − |
| Soluble pigments | − | − | − | − |
| Spore shape | oblong | ND[c] | ND | oblong |
| Spore surface | smooth | ND | ND | smooth |
| Survival at 50° C., 8 hrs. | + | + | + | + |
| Temperature range °C. | 45 | 45 | 37 | 45 |
| Urease production | + | + | + | + |

[a] + = culture has trait; − = culture does not have trait
[b] NG = not grown out
[c] ND = not done Table V summarizes the characteristics in which the A54145 strains differ.

TABLE V

Comparison of Differences in the A54145 Strains

| Characteristic | A54145.1 | A54145.2 | A54145.3 |
|---|---|---|---|
| Aerial hyphae production | fair | fair | poor |
| Esculin degradation | + | + | − |
| Fructose utilization | + | − | − |
| Gelatin liquefaction | + | + | − |
| Lactose utilization | + | − | + |
| Nitrate reduction | + | + | − |
| % NaCl tolerance | 6 | 4 | 6 |
| Reverse side color | lt. brn | lt. brn | dk. brn |
| Temperature range - °C. | 45 | 45 | 37 |

Cell-wall Analysis

Hydrolyzed whole cells of the original isolate A54145 contained LL-diaminopimelic acid with no meso isomer present. This is indicative of a Type I cell wall [M. P. Lechevalier, "Identification of Aerobic Actinomycetes of Clinical Importance," *J. Lab Clin. Med.* 71:934–944 (1968).

A qualitative analysis of whole-cell methanolysates indicated that A54145.1 does not contain mycolic acids. The other strains were not analyzed; these characteristics are known not to change with mutation [M. P. Lechevalier, A. C. Horan and H. Lechevalier, "Lipid Composition in the Classification of Nocardiae and Mycobacteria," *J. Bacteriol.* 105(1):313–318 (1971)].

Species Determination

The chemotaxonomic information plus the general cultural and morphological characteristics were consistent with the assignment of strain A54145.1 to the genus Streptomyces.

Six species selected from the published literature were similar to culture A54145.1:
*Streptomyces cremeus**
*Streptomyces roseolus**

*Streptomyces termitus*\*\*
*Streptomyces fradiae*\*
*Streptomyces roseus*\*
*Streptomyces roseosporus*\*\*\*

\*E. B. Shirling and D. Gottlieb, "Comparative Description of Type Strains of Streptomyces" *Int. J. Syst. Bacteriol.* 18(2):69–189 (1968)
\*\*ibid. 19(4):375–512 (1969)
\*\*\*ibid 18(4):279–392 (1968)

These cultures belong in the red color series, have Retinaculum-apertum and Rectus-flexibilis sporophore morphology, smooth spore-surface ornamentation, lack melanoid and distinctive pigments, and have a carbon-utilization pattern and other cultural characteristics similar to those of culture A54145.1.

The six selected species were grown simultaneously with A54145.1, A54145.2 and A54145.3 to obtain direct laboratory comparisons. Two cultures, *S. fradiae* and *S. roseosporus*, were observed to be most similar to A54145.1. Of these two, *S. roseosporus* did not have a very close cultural match to A54145.1 On many of the media *S. roseosporus* was in the white color series *S. roseosporus* generally grew better and produced more abundant aerial mycelia than A54145.1, except on Czapek's solution agar where *S. roseosporus* had no growth. *S. roseosporus* was in the Rectus-flexibilis morphology series, while A54145.1, although having the (RF) type of morphology, was predominantly of the Retinaculum-apertum type. Thus, although *S. roseosporus* had many physiological characteristics like those of A54145.1; the differences in cultural and morphological characteristics precluded assignment of A54145.1 as a strain of *S. roseosporus*.

*S. fradiae* was very similar to A54145.1 culturally, morphologically and physiologically. Both cultures had an excellent aerial hyphae color match, similar reverse color and absence of soluble pigments. *S. fradiae* and A54145.1 had the same sporophore morphology, short spore chains, spore shape, and smooth spore-surface ornamentation.

Physiological characteristics were in good agreement, except for the antibiotic-resistance pattern, degradation of hypoxanthine, production of $H_2S$, and tolerance to NaCl. A summary of the differences and similarities between strain A54145.1 and *S. fradiae* is given in Table VI.

TABLE VI

Comparison of Strain A54145.1 and *S. fradiae*

| Similarities | Differences |
| --- | --- |
| absence of melanoid pigments | antibiotic resistance |
| aerial spore mass color | $H_2S$ production |
| carbon utilization | hypoxanthine degradation |
| catalase production | NaCl tolerance |
| cultural characteristics | |
| degradation profile | |
| gelatin liquefaction | |
| morphology | |
| nitrate reduction | |
| phosphatase production | |
| skim milk reaction | |
| survival at 50° C., 8 hr. | |
| temperature range | |
| urease production | |

These comparisons indicate that culture A54145.1 is very similar to *S. fradiae*. Therefore culture A54145.1 is classified as a strain of *Streptomyces fradiae* (Waksman and Curtis 1916) Waksman and Henrici 1948. *S. fradiae* is recognized in the Approved Lists of Bacterial Names [V. B. D. Skerman, V. McGowan, and P. H. A. Sneath (ed.), "Approved Lists of Bacterial Names," *Int. J. Syst. Bacteriol.* 30:225–420 (1980)] and consequently is a validly published species. Cultures A54145.2 and A54145 3 are classified as *S. fradiae* mutants derived from A54145.1.

As is the case with other organisms, the characteristics of the A54145-producing cultures *Streptomyces fradiae* NRRL 18158, NRRL 18159 and NRRL 18160 are subject to variation. Thus, progeny of these strains, e.g., spontaneous and induced mutants may be obtained by methods known in the art. Spontaneous mutants can be obtained by natural selection, or mutants can be induced by treatment with various known physical and chemical mutagens such as ultraviolet light, X rays, gamma rays and chemicals such as N-methyl-N'-nitro-N-nitrosoguanidine. Mutants of the *Streptomyces fradiae* strains NRRL 18158, NRRL 18159 and NRRL 18160 which retain the characteristic of producing recoverable amounts of the A54145 antibiotics are part of this invention.

The culture medium used to grow the A54145-producing *Streptomyces fradiae* strains can be any one of a number of media. For economy in production, optimal yield, and ease of product isolation, however, certain culture media are preferred. For example, preferred carbon sources are glucose, maltose, galactose, methyl oleate and peanut oil, although corn starch, potato dextrin, corn oil, cottonseed oil, soybean oil and the like can also be used.

Preferred nitrogen sources are soybean grits, soybean flour or an enzymatic hydrolysate of soybeans. Enzyme-hydrolyzed casein, peanut meal, fish meal, cottonseed meal, and the like are also useful nitrogen sources.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism.

Small amounts (i.e. 0.2 ml/L) of an antifoam agent such as polypropylene glycol may be added to large scale fermentation media if needed.

For production of substantial quantities of the A54145 antibiotics, submerged aerobic fermentation in tanks is preferred. Small quantities may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger vessel. The vegetative inoculum medium can be the same as that used for larger fermentations, but other media are also suitable.

The A54145 antibiotics are produced by the *Streptomyces fradiae* strains when grown at temperatures between about 20° and about 35° C. A good temperature for A54145 production appears to be from about 25° C. to about 29° C.

As is customary in submerged aerobic culture processes, sterile air is blown into the vessel from the bottom while the medium is stirred with conventional turbine impellors. In a fully baffled 165-liter fermentor containing approximately 115 liters of broth, an aeration rate of 0.25 v/v/m with an agitation rate of 150-200 rpm is sufficient to maintain the level of dissolved oxygen at or above 30% of air saturation.

Production of antibiotic A54145 can be followed during the fermentation by testing samples of the broth for antibiotic activity against organisms known to be sensitive to the antibiotic. One assay organism useful in testing for antibiotic A54145 is *Bacillus subtilis*. The bioassay is conveniently performed by the agar-well plate test.

In Boeck's application (attorney Docket No. X-7252), supra, he describes improved processes for preparing the A54145 components. One process comprises feeding a $C_4$-$C_{18}$-alkanoic or alkenoic acid or alcohol, or an ester or salt thereof, to an A-54145-producing culture during its fermentation and recovering the A54145 components. This process provides significantly increased product yields of A54145 components.

In this process the alkyl portion of the alkanoic or alkenoic acid or alcohol (the substrate) used can be a straight or branched chain. The straightchain acids or alcohols, or their esters or salts, are recommended because of availability and lower cost. An especially preferred substrate is n-decanoic acid and its esters and salts.

When using an alkanoic acid ester, the $C_1$-$C_4$-alkyl esters are preferred. In such an ester the $C_1$-$C_4$-alkyl group may also be straight or branched.

Representative suitable salts of alkanoic or alkenoic acids which may be used in this process include those formed from alkali metals and alkaline-earth metals such as sodium, potassium, lithium, cesium, rubidium, barium, calcium and magnesium. Suitable amine salts include the ammonium and the primary, secondary and tertiary $C_1$-$C_4$-alkyl-ammonium and hydroxy-$C_2$-$C_4$-alkyl-ammonium salts.

For this process it is preferable to add the substrate to the fermentation in the form of a sterile solution. For example, n-decanoic acid is a solid at room temperature, whereas its ethyl ester is a liquid. Thus, the ethyl ester is preferred because the acid must be dissolved in a compatible liquid, such as oleic acid or methyl oleate, for efficient feeding. Oleic acid is a particularly useful solvent for this purpose, although other solvents such as ethanol, ethyl acetate and $C_1$-$C_4$ esters of unsaturated fatty acids can be used. Those substrates which are suitably fluid at fermentation temperatures may be added directly and are, therefore, preferred.

The rate of addition of the substrate to the fermentation must be low enough to avoid producing a toxic effect on the fermentation, but high enough to increase the yield of the desired compound. Rates of addition of about 0.5 to about 4 mL of substrate per liter of fermentation broth per day can be used. A rate of from about 1.5 to about 3 mL of substrate per liter of fermentation broth per day is preferred.

The substrate is added to the growing A54145-producing culture during the production stage of the fermentation, beginning at from about 20 to about 26 hours and continuing until the fermentation is terminated. The substrate can be added by various methods. It is preferable, however, to add it by a method which best approaches a steady flow.

Another improved process for preparing A54145 compounds described in Boeck's application comprises feeding glucose at a rate from about 6 to about 9 grams/liter/day to an A54145-producing culture, starting from about 18 to about 24 hours after initiating the production stage and continuing throughout its fermentation. The improvement obtained by this process is illustrated in Table VII, which compares the results obtained by standard methods with results obtained using this process.

TABLE VII

Effect of Continuous Glucose Feed on A54145 Biosynthesis

| Glucose Level(%) | Glucose Addition Method | A54145 Yield (mcg/mL) |
|---|---|---|
| 4 | Included at time of medium make-up | 520 |
| 4 | Continuous feed from day 1 to day 8[a] | 1370 |

[a]Beginning 20 hours after initiating the production stage

As the results in Table VII indicate, glucose feeding increases final A54145 yield by at least 150%.

In the continuous glucose feed process, the rate of addition of the glucose must be low enough to avoid toxic affects on the fermentation, but high enough to cause a significant increase in the yield of A54145 compound. A rate of about 6 to about 9 grams of glucose/liter of fermentation/day is recommended, but a rate of about 7.5 g/L/day is preferred for this process.

A third method for increasing product yields of A54145 components which Boeck describes comprises feeding an enzymatic soy digest to the fermentation at a rate of from about 2 to about 4 grams of soy digest/liter of fermentation broth/day to an A54145-producing culture, starting from about 90 to about 120 hours after initiating the production stage, and continuing throughout its fermentation.

Each of the Boeck processes can be carried out over a temperature range of from about 20° to about 34° C. Temperature affects the amount of total antibiotic produced and the type of nucleus and side chain produced. Thus, the temperature of the fermentation should be adjusted appropriately in order to obtain optimum yields of the desired product. Table VIII summarizes temperature effects on A54145 production which were observed in fermentation studies in which only the temperature was varied.

TABLE VIII

EFFECT OF TEMPERATURE ON A54145 NUCLEUS AND ACYL-CHAIN BIOSYNTHESIS IN A STIRRED 165-L BIOREACTOR

| Temperature (°C.) | Total Antibiotic (mcg/mL) | Nuclei (%) | | | | Acyl Chains (%)[a] | | |
|---|---|---|---|---|---|---|---|---|
| | | A | B | C | F | $iC_{10}$ | $nC_{10}$ | $aC_{11}$ |
| 21 | 1015 | 60 | 31 | — | 9 | 79 | 15 | 6 |
| 25 | 1582 | 62 | 30 | — | 8 | 74 | 18 | 8 |
| 29 | 1623 | 39 | 51 | 3 | 6 | 64 | 21 | 14 |
| 31 | 1341 | 32 | 59 | 2 | 6 | 59 | 23 | 17 |
| 33 | 923 | 19 | 73 | 2 | 6 | 60 | 23 | 16 |

[a]$iC_{10}$ = 8-methylnonanoyl
$nC_{10}$ = n-decanoyl
$aC_{11}$ = 8-methyldecanoyl Following its production under submerged aerobic fermentation conditions, antibiotic A54145 can be recovered from the fermentation medium by methods used in the fermentation art. The antibiotic activity produced during fermentation of the A54145-producing organisms occurs mainly in the broth. Maximum recovery of antibiotic A54145 is accomplished, therefore, by initially filtering the medium to separate the broth from the mycelial mass. The filtered broth can then be treated separately by a variety of techniques to give the antibiotic A54145.

A preferred technique for treating the filtered broth involves first adsorbing it on a resin such as Diaion HP-20, discarding the broth which remains, washing the resin with water and then extracting the resin with a suitable solvent such as, for example, aqueous acetonitrile. The extracting solvent can then be evaporated under vacuum to give antibiotic A54145.

Antibiotic A54145 can be further purified and separated into its individual components by a number of procedures. One such procedure involves ion-exchange chromatography.

Separation of antibiotic A54145 into its individual components can be followed by TLC or HPLC. One convenient analytical HPLC system is:

Analytical HPLC System for A54145 Components

Column: 4.6-mm × 25-cm silica gel (Zorbax C8, Dupont)

Mobile Phase: acetonitrile/water containing 0.2% triethylamine and adjusted to pH 3 with phosphoric acid (35:65)

Detection: UV at 223 nm

Flow Rate: 2 mL/min

A54145 components A-F have the following approximate retention times in this system:

| A54145 Factor | Retention Time (min) |
|---|---|
| A | 12.1 |
| $A_1$ | 13.1 |
| B | 14.9 |
| $B_1$ | 13.7 |
| C | 17.0 |
| D | 19.6 |
| E | 22.4 |
| F | 9.4 |

Alternatively, the culture solids, including medium constituents and mycelium, can be used without extraction or separation, but preferably after removal of water, as a source of antibiotic A54145. For example, after production of the antibiotic, the whole fermentation broth can be dried by lyophilization, by drum-drying, or by azeotropic distillation and drying. The dried broth is then mixed directly into feed premix.

The A54145 antibiotics inhibit the growth of pathogenic bacteria. For example, Table IX shows the inhibitory concentrations (MIC's) at which the A54145 antibiotics inhibit certain organisms. The MIC's in Table IX were determined by conventional agar-dilution assays.

TABLE IX

Antibacterial Activity of the A54145 Antibiotics[a]

| Test Organism | A | B | C | D | E | F | $A_1$ | $B_1$ |
|---|---|---|---|---|---|---|---|---|
| Staphylococcus aureus X1.1 | 8 | 2 | 2 | 4 | 1 | 16 | 4 | 2 |
| Staphylococcus aureus V41 | 8 | 2 | 2 | 4 | 2 | 16 | 4 | 2 |
| Staphylococcus aureus X400 | 8 | 2 | 2 | 4 | 2 | 16 | 8 | 2 |
| Staphylococcus aureus S13E | 8 | 2 | 2 | 4 | 2 | 16 | 8 | 2 |
| Staphylococcus epidermidis EPI1 | 4 | 2 | 2 | 2 | 1 | 16 | 4 | 1 |
| Staphylococcus epidermidis 222 | 4 | 2 | 1 | 2 | 1 | 8 | 4 | 1 |
| Streptococcus pyogenes C203 | 2 | 0.5 | 0.5 | 0.5 | 0.25 | 4 | 1 | 0.5 |
| Streptococcus pneumoniae Park1 | 8 | 2 | 2 | 4 | 1 | 8 | 4 | 2 |
| Streptococcus sp. group D X66 | 16 | 4 | 4 | 4 | 2 | 16 | 16 | 8 |
| Streptococcus sp. group 2041 | 64 | 8 | 4 | 32 | 4 | >32 | 32 | 32 |

[a]MIC in mcg/mL

The in vitro activity of the A54145 antibiotics is stimulated by the presence of calcium ions. For example, the in vitro activity of A54145A against Staphylococcus aureus 209P and Streptococcus faecalis ATCC 29212 was stimulated about 100 times by the presence of $Ca^{++}$ (50 mg/mL).

The A54145 antibiotics have shown in vivo antimicrobial activity against experimentally-induced infections in laboratory animals. When two doses of test compound were administered to mice experimentally infected with Streptococcus pyogenes or Staphylococcus aureus, the activity observed was measured as an $ED_{50}$ value [effective dose in mg/kg to protect 50% of the test animals: see Warren Wick, et al. J. Bacteriol. 81 233–235 (1961)]. The $ED_{50}$ values observed for A54145A and A54145B are given in Table X.

TABLE X $ED_{50}$ Values for A54145 Components in Mice[a]

| Infecting Organism | $ED_{50}$ Value[b] | | |
|---|---|---|---|
|  | A54145A | A54145B | $A54145A_1$ |
| Streptococcus pyogenes | 2.4[c] | 0.94 | 5.0 |
| Staphylococcus aureus | 3.3 | —[d] | — |

[a]Administered subcutaneously
[b]mg/kg × 2; doses given 1 and 4 hours hours post-infection
[c]Average of two tests with individual values of 1.6 and 3.1
[d]Not done The A54145 antibiotics improve growth performance in animals. The antibiotics are especially effective in fowl, such as chickens and turkeys, but are also effective in other animals such as swine. This effect of the antibiotics is exemplified by in vivo tests in which A54145A and A54145B increased weight gains in chickens and A54145A improved the feed/gain ratio in pigs.

Tables XI-XIII summarize the results of the tests in chickens. In the tests, the compounds were given to chicks at the concentrations indicated in the feed. The test period was the 7-day period from 7–14 days of age of the birds. Growth performance (weight gain, feed consumption and feed efficiency) was compared to that of contemporary controls.

TABLE XI

Effect of A54145 on Chick Growth

| Treatment[a] | Conc. (g/ton) | Weight Gain | | Feed/Gain | |
|---|---|---|---|---|---|
|  |  | Amt. (g) | % Impr[b] | Ratio | % Impr |
| Control | — | 339 | — | 2.042 | — |
| A54145 | 5 | 330 | −2.7 | 2.090 | −2.4 |
| A54145 | 10 | 364 | 7.4 | 1.982 | 2.9 |
| A54145 | 20 | 369 | 8.8 | 1.988 | 2.6 |
| Dried A54145 | 10 | 417 | 23.0 | 1.799 | 11.9 |

TABLE XI-continued

Effect of A54145 on Chick Growth

| Treatment[a] | Conc. (g/ton) | Weight Gain Amt. (g) | Weight Gain % Impr[b] | Feed/Gain Ratio | Feed/Gain % Impr |
|---|---|---|---|---|---|
| Whole Broth Dried A54145 | 10 | 419 | 23.6 | 1.818 | 8.3 |
| Broth Filtrate Dried A54145 HP-20 Eluate | 10 | 444 | 31.0 | 1.776 | 13.0 |

[a] 10 groups, 5 birds in each
[b] Percent improvement relative to the control mean

TABLE XII

Effect of A54145A on Chick Growth

| Treatment[a] | Conc. (g/ton) | Weight Gain Amt. (g) | Weight Gain % Impr[b] | Feed/Gain Ratio | Feed/Gain % Impr |
|---|---|---|---|---|---|
| Control | — | 133 | — | 1.738 | — |
| A54145A | 20 | 168 | 26.3 | 1.546 | 11.0 |

[a] 10 groups, 7 birds in each
[b] Percent improvement relative to the control mean

TABLE XIII

Effect of A54145B and A54145B$_1$ on Chick Growth[a]

| Treatment[b] | Conc. (g/ton) | Weight Gain Amt. (g) | Weight Gain % Impr[c] | Feed/Gain Ratio | Feed/Gain % Impr. |
|---|---|---|---|---|---|
| Control | — | 315 | — | 2.013 | — |
| A54145B | 5 | 341 | 8.3 | 1.887 | 6.3 |
| A54145B | 10 | 392 | 24.4 | 1.730 | 14.1 |
| A54145B | 20 | 402 | 27.6 | 1.785 | 11.3 |
| A54145B$_1$ | 5 | 326 | 3.5 | 1.906 | 5.3 |
| A54145B$_1$ | 10 | 358 | 13.7 | 1.860 | 7.4 |
| A54145B$_1$ | 20 | 448 | 42.2 | 1.686 | 16.2 |

[a] In this study, antibiotic A54145 (which contained factor A, but did not contain factors B or B$_1$) did not show significant weight gain or feed/gain improvement
[b] 5 Birds in each group; 5 groups for treated; 20 groups for control
[c] Percent improvement relative to the control mean Table XIV summarizes the results of the test in pigs. In this test, a total of 145 barrows and gilts, averaging 22 pounds starting weight, were used to determine the effect of various dosages of A54145 on the growth performance of starter pigs. The pigs were fed an 18% crude protein corn-soy diet and were housed in a completely enclosed building with wire mesh floors elevated over a flush floor. The effect of the treatments on performance was studied for a 28-day trial period.

As Table XIV shows, A54145 promoted average daily gain when administered at rates of 10, 40 and 80 ppm.

TABLE XIV

Effect of A54145 on the Growth Performance of Starter Pigs[a,b]

| Treatment | Level (ppm) | No. Exp. Units[c] | No. Pigs[d] | Average Daily Gain (lbs) | Average Daily Feed (lbs) | Feed/Gain Ratio |
|---|---|---|---|---|---|---|
| Control | — | 4 | 24 | 0.92 | 2.11 | 2.29 |
| A54145 | 5 | 4 | 23 | 0.92 (—) | 2.08 (−1.4) | 2.24 (−2.2) |
|  | 10 | 4 | 24 | 0.96 (+4.3) | 2.17 (+2.8) | 2.25 (−1.7) |
|  | 20 | 4 | 23 | 0.91 (—) | 2.05 (−2.8) | 2.23 (−2.6) |
|  | 40 | 4 | 23 | 0.96 (+4.3) | 2.15 (+1.9) | 2.23 (−2.6) |
|  | 80 | 4 | 24 | 0.98 (+6.5) | 2.09 (−1.0) | 2.12 (−7.4) |

[a] Initial starting weight = 22 lbs; 5-6 pigs/pen
[b] Figures in parentheses are percent change from control.
[c] Exp. unit = pen of pigs
[d] Three pigs were removed from this trial due to death or disease.

The A54145 antibiotics are typically effective in improving growth performance in animals when administered with feeds at a rate of from about 0.05 to about 100 grams of A54145 antibiotic per ton of feed (0.055 to 110 ppm). A preferred rate is from about 0.05 to about 50 ppm, and an especially preferred rate is from about 1 to about 20 g/ton.

The A54145 antibiotics can be administered to animals orally or parenterally. The most practical way to administer the antibiotic is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A54145 antibiotic directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing an A54145 antibiotic.

The A54145 antibiotics may be formulated for parenteral administration by methods recognized in the veterinary pharmaceutical art. Effective injectable compositions containing the A54145 antibiotics may be in either suspension or solution form. In the solution form, the antibiotic compound is dissolved in a physiologically acceptable carrier. Such carriers comprise a suitable solvent, preservatives such as benzyl alcohol, if needed, and buffers. Useful solvents include, for example, water, alcohols, glycols, or inert oils such as vegetable oils or highly refined mineral oils.

Injectable suspension compositions are prepared using a nonsolvent for the compound with adjuvants, as a carrier. The nonsolvent can be, for example, a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In order to illustrate more fully the operation of this invention, the following examples are provided. In these examples the following numbers will be used to represent specific solvent systems:

| No. | Solvent | Ratio |
|---|---|---|
| 1 | Pyridine/HOAc/H$_2$O | 1:1:98 |
| 2 | Pyridine/HOAc/H$_2$O/CH$_3$CN | 1:1:88:10 |
| 2a | " | 1:1:87:11 |
| 2b | " | 1:1:86:12 |
| 2c | " | 1:1:83:15 |
| 2d | " | 1:1:82:16 |
| 2e | " | 1:1:78:20 |
| 2f | " | 1:1:73:25 |
| 2g | " | 1:1:70.5:27.5 |
| 2h | " | 1:1:68:30 |
| 2i | " | 1:1:67:31 |
| 2j | " | 1:1:66:32 |
| 2k | " | 1:1:65:33 |
| 2m | " | 1:1:63:35 |
| 3a | Pyridine/HOAc/H$_2$O/CH$_3$CN/MeOH | 1:1:70:18:10 |
| 3b | " | 1:1:68:20:10 |
| 3c | " | 1:1:63:25:10 |
| 3d | " | 1:1:61:27:10 |
| 3e | " | 1:1:58:30:10 |
| 3f | " | 1:1:56:32:10 |
| 3g | " | 1:1:53:35:10 |
| 3h | " | 1:1:68:25:5 |
| 3i | " | 1:1:73:15:10 |
| 3j | " | 1:1:60.5:25:12.5 |
| 3k | " | 1:1:71:20:7 |
| 4 | CH$_3$CN/H$_2$O | 1:1 |
| 4a | " | 15:85 |
| 5 | CH$_3$OH/H$_2$O | 1:1 |

EXAMPLE 1

Preparation of Antibiotic A54145 with *Streptomyces fradiae* A54145.1

A. Shake-flask Fermentation of A54145.1

The culture *Streptomyces fradiae* NRRL 18158, either as a lyophilized pellet or as a suspension maintained in liquid nitrogen, is used to inoculate 50 mL of a vergetative medium having the following composition:

| Vegetative Medium I | |
|---|---|
| Ingredient | Amount (g/L) |
| Glucose | 15.0 |
| Potato dextrin | 20.0 |
| Soybean grits | 15.0 |
| Corn steep liquor | 10.0 |
| Yeast extract | 1.0 |
| CaCO$_3$ | 5.0 |
| Tap water | q.s. 1 liter |
| (Adjust the pH of the medium from ~6.1 to ~6.5 with NaOH before sterilizing; post-sterilization pH ~7) | |

The inoculated first-stage medium is incubated in a 250-mL Erlenmeyer flask at 30° C. for about 48 hours on a shaker orbiting in a two-inch (5.08 cm) circle at 250 rpm.

This incubated first-stage medium (1 mL) is used to inoculate 50 mL of a production medium having the following composition:

| Production Medium I | |
|---|---|
| Ingredient | Amount (g/L) |
| Glucose | 45 |
| Soybean grits | 35 |
| Blackstrap molasses | 3 |
| CaCO$_3$ | 2.5 |
| Tap water | q.s. 1 liter |
| (Presterilization pH ~6.9; post-sterilization pH ~6.8) | |

The inoculated production medium is incubated in a 250-mL wide-mouth Erlenmeyer flask at 25° C. for 6 to 7 days on a shaker orbiting in a two-inch circle at 250 rpm.

B. Tank Fermentation of A54145.1

In order to provide a larger volume of inoculum, 10 mL of incubated vegetative medium, prepared as described in Section A, is used to inoculate 400 mL of a second-stage growth medium having the same composition as that of the first-stage vegetative medium. This second-stage vegetative medium is incubated in a two-liter wide-mouth Erlenmeyer flask for about 24 hours at 30° C. on a shaker orbiting in a two-inch circle at 250 rpm.

Incubated second-stage vegetative medium (800 mL) thus prepared is used to inoculate 115 liters of sterile production medium, prepared as described in Section A, except that 0.2 g/L of a silicon antifoam such as Sag-471 (Union Carbide) is added. The inoculated production medium is allowed to ferment in a 165-liter stirred fermentation tank for 6 to 7 days at a temperature of 25° C. Low airflow (0.25 v/v/m) and low rpm (200-300) in the stirred vessel maintain a dissolved oxygen level above 30% of air saturation. The pH is not allowed to rise above 7.5.

EXAMPLE 2

Preparation of Antibiotic A54145 with *Streptomyces fradiae* A54145.2

A. Shake-flask Fermentation of A54145.2

Shake-flask fermentation is carried out as in Example 1, Section A, with the following exceptions:

(1) the culture is *Streptomyces fradiae* NRRL 18159;

(2) the vegetative medium has the following composition:

| Vegetative Medium II | |
|---|---|
| Ingredient | Amount (g/L) |
| Glucose | 10 |
| Potato starch | 30 |
| Soybean flour | 20 |
| Defatted cottonseed flour | 20 |
| CaCO$_3$ | 2 |
| Tap water | 1 liter |

(3) the vegetative medium is incubated at 25° C.; and (4) the production medium has the following composition:

| Production Medium II | |
|---|---|
| Ingredient | Amount (q/L) |
| Glucose | 25.0 |
| Soybean grits | 18.75 |
| Blackstrap molasses | 3.75 |

-continued

Production Medium II

| Ingredient | Amount (q/L) |
| --- | --- |
| Casein | 1.25 |
| CaCO$_3$ | 3.125 |
| Sodium acetate | 8.0 |
| Tap water | q.s. to 1 L |
| (Pre-sterilization pH ~6.9; post-steriliza- tion pH ~6.8) | |

B. Tank Fermentation of A54145.2

Incubated vegetative medium prepared as described in Section A is used, and the procedures of Example 1, Section B, are followed with these exceptions:

(1) the amount of incubated vegetative medium used to inoculate the second-stage growth medium is 8 mL;

(2) the amount of second-stage medium used to inoculate the production medium is 2 L;

(3) the air flow is 0.125 v/v/m; and (4) the pH is allowed to rise above 7.5.

EXAMPLE 3

Preparation of Antibiotic A54145 with *Streptomyces fradiae* A54145.3

The procedures of Example 2, Sec. B, are followed except that the culture used is *Streptomyces fradiae* NRRL 18160 and the production medium has the following composition:

Production Medium III

| Ingredient | Amount (g/L) |
| --- | --- |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |
| Tap water | q.s. to 1 liter |

EXAMPLE 4

Isolation of Antibiotic A54145

Whole fermentation broth from two 100-L tanks (217 L), prepared as described in Example 2, was filtered through a filter press with 3% filter aid (Hyflo Super-Cel, Manville Products, Lompoc CA). The filtrate (185 L) was adjusted to pH 6.4, using 5 N HCl. Diaion HP-20 resin (20 L) was added to the filtrate. The initial effluent (185 L) and a water wash (60 L) were discarded. The resin was then eluted as follows:

| Eluate | Solvent No. | Amount |
| --- | --- | --- |
| 1 | 4a | 40 L |
| 2 | 4 | 30 L |
| 3 | 4 | 30 L |

Eluate 1 was discarded.

Eluates 2 and 3 were combined and chromatographed on 2 L of IRA-68(OAc$^-$) (2.5"×32"). The initial effluent (60 L), a wash with solvent No. 4 (10 L) and an eluate with 0.1N HOAc:CH$_3$CN (1:1, 10 L) were discarded. The column was then eluted with 14 L of 1.0N HOAc:CH$_3$CN (1:1). This fraction was concentrated under vacuum and lyophilized to give 101.1 g of antibiotic A54145.

EXAMPLE 5

The procedure of Example 4 was repeated, giving 211 L of whole broth, 170 L of filtrate and 127.7 g of antibiotic A54145.

EXAMPLE 6

The procedure of Example 4 was repeated, giving 233 L of whole broth, 170 L of filtrate and 96.1 g of antibiotic A54145.

EXAMPLE 7

Effect of Lipid Precursors, Media and Feeding Enzymatic Soy Digest on A54145 Production A54145 fermentations were carried out as in Example 3, but using the following three production media, with and without lipid feeding:

Medium A

| Ingredient | Amount (g/L) |
| --- | --- |
| Glucose | 25.0 |
| Soybean grits | 15.0 |
| Blackstrap molasses | 3.0 |
| Acid-hydrolyzed casein | 1.0 |
| CaCO$_3$ | 2.5 |
| Tap water | q s. 1 liter |
| (Pre-sterilization pH ~7.0; post-sterilization pH ~7.1) | |

Medium B

| Ingredient | Amount (g/L) |
| --- | --- |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |
| Potato dextrin | 30.0 |
| Tap water | q.s. to 1 liter |

Medium C

| Ingredient | Amount (g/L) |
| --- | --- |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |
| Tap water | q s. to 1 liter |

Medium D

Medium C with an enzymatic-soy-digest (Hy Soy, Sheffield Products, Norwich N.Y.) feeding.

Table XV summarizes the results of these studies.

TABLE XV

EFFECT OF LIPID PRECURSORS AND MEDIA ON YIELDS AND FACTOR SIDE CHAINS OF A54145 IN A STIRRED 165-L BIOREACTOR

| Medium | Lipid Precursor[a] | Total Antibiotic (mcg/mL) | Factor Side Chains (%)[b] | | |
|---|---|---|---|---|---|
| | | | $iC_{10}$ | $nC_{10}$ | $aC_{11}$ |
| A | — | 97 | 68 | 20 | 12 |
| A | $nC_{10}$ | 179 | 20 | 79 | 1 |
| B | — | 570 | 70 | 17 | 13 |
| B | $nC_{10}$ | 1046 | 7 | 91 | 2 |
| C | — | 1100 | 76 | 14 | 10 |
| C | $nC_{10}/C_{18:1}$ | 2316 | 19 | 74 | 7 |
| D | $nC_{10}/C_{18:1}$ | 3570 | 21 | 71 | 8 |

[a] $nC_{10}$ = ethyl caprate
$nC_{10}/C_{18:1}$ = n-decanoic acid in methyl oleate (1:1)
[b] $iC_{10}$ = 8-methylnonanoyl
$nC_{10}$ = n-decanoyl
$aC_{11}$ = 8-methyldecanoyl

EXAMPLE 8

Effect of Amino-Acid Enrichment on A54145 Production

A54145 fermentations were carried out as in Example 2, Section A, but using the culture used in Example 3 and the following production medium:

| Ingredient | Amount (g/L) |
|---|---|
| Glucose | 30.00 |
| Soybean flour | 25.0 |
| Blackstrap molasses | 5.0 |
| CaCO$_3$ | 4.0 |
| Fe(SO$_4$).(NH$_4$)$_2$SO$_4$.6H$_2$O | 0.6 |
| Tap water | q.s. 1 liter |

Different amino acids were added to study their effects on the A54145 nuclei and acyl side chains produced. Table XVI summarizes the results of these studies.

TABLE XVI

EFFECT OF AMINO ACID ENRICHMENT ON BIOSYNTHESIS OF A54145 NUCLEI AND ACYL CHAINS IN SHAKEN FLASKS

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | | 100[c] | 50 | 39 | 1 | 10 | 65 | 18 | 17 |
| L-Val | .03 | 32 | 32 | 20 | 2 | 54 | 98 | 0 | 2 |
| L-Leu | .02 | 56 | 42 | 40 | 2 | 16 | 76 | 7 | 17 |
| L-Ile | .04 | 73 | 48 | 47 | 2 | 0 | 16 | 18 | 66 |
| L-Glu | .02 | 85 | 49 | 39 | 1 | 11 | 63 | 20 | 16 |
| L-Asp | .005 | 134 | 56 | 34 | 1 | 10 | 64 | 19 | 17 |
| L-Tyr | .02 | 59 | 12 | 76 | 1 | 11 | 67 | 18 | 15 |

[a] Percent of total produced
[b] $iC_{10}$ = 8-methylnonanoyl
$nC_{10}$ = n-decanoyl
$aC_{11}$ = 8-methyldecanoyl
[c] 550 mcg/mL Table XVII summarizes the results of a similar study of the effect L-tyrosine has on A54145 production. Thus study was made in a 115-liter fermentation run.

TABLE XVII

EFFECT OF L-TYROSINE ENRICHMENT ON BIOSYNTHESIS OF A54145 NUCLEI IN A STIRRED 165-L BIOREACTOR

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | — | 100[c] | 19 | 78 | 1 | 2 | 19 | 74 | 7 |
| L-Tyr | 0.01 | 102 | 10 | 87 | 1 | 1 | 28 | 67 | 5 |

[a] Percent of total produced
[b] $iC_{10}$ = 8-methylnonanoyl
$nC_{10}$ = n-decanoyl
$aC_{11}$ = 8-methyldecanoyl
[c] 3200 mcg/mL Comparing the results in Tables XVI and XVII shows that the scale of the fermentation affects the amount of a) total antibiotic produced, b) nuclei produced and c) acyl side chains produced. Adding L-tyrosine decreased total antibiotic production in the shaken-flask fermentation, but did not adversely affect production in the tank fermentation. The unsupplemented shaken-flask fermentation produced more A nucleus and more $iC_{10}$ side chain product, whereas the unsupplemented tank fermentation produced more B nucleus and more $nC_{10}$ side chain. L-tyrosine increased the percentage of B-nucleus produced in both shaken flasks and tanks, but the effect was more pronounced in flasks.

Adding L-valine or L-leucine increased the percentage of F nucleus produced and the percentage of $iC_{10}$ side chain product. This effect was more pronounced with L-valine.

Adding L-isoleucine increased the percentage of both B nucleus and $aC_{11}$ side chain produced.

EXAMPLE 9

An A54145 fermentation was carried out as described in Example 3 except that the following production medium was used:

| Ingredient | Amount (g/L) |
|---|---|
| Soybean flour | 30.0 |
| Blackstrap molasses | 5.0 |
| Glucose | 3.0 |
| Fe(SO$_4$).(NH$_4$)$_2$SO$_4$.6H$_2$O | 0.6 |
| Deionized water | q.s. 1 liter |

Antifoam agents were added, and the pH was adjusted from ~6.2 to ~7.2 with 5N NaOH.

Beginning about 23 hours after the fermentation was initiated, glucose was fed to the fermentation at a rate of approximately 6.5 g/L/day. Beginning at about 25 hours after the fermentation was initiated, a sterile solution consisting of decanoic acid and oleic acid (1:1, v/v) was fed to the fermentation at a rate of approximately 6.0 mL/L/day.

At about 117 hours after the fermentation was initiated, a feeding of enzymatic soy digest was initiated and continued at a rate of about 3.0 g/L/day.

The yield of A54145 from the fermentation after about 280 hours was 3969 mcg/mL. This yield is substantially greater than the yield of about 500 mcg/mL ordinarily obtained using similar conditions, but without the glucose, enzymatic soy digest and decanoic acid feeds used in this fermentation.

EXAMPLE 10

Another series of fermentations was carried out using the procedures of Example 7 with Medium C, but adding different C$_4$–C$_{18}$-alkanoic acids and esters to enhance A54145 production. The results of these studies are shown in Table XVIII.

TABLE XVIII

EFFECT OF LIPID PRECURSORS ON BIOSYNTHESIS OF A54145 SIDE CHAINS IN A STIRRED 165-L BIOREACTOR

| Precursor | RQ$^a$ Calcd.$^d$ | RQ$^a$ Found$^e$ | Total A54145 (%) | Known Side Chains Percent of Total iC$_{10}$ | nC$_{10}$ | aC$_{11}$ | New Analogs$^{b,c}$ C$_6$A | C$_6$B | C$_8$A | C$_8$B | C$_9$A | C$_9$B |
|---|---|---|---|---|---|---|---|---|---|---|---|---|
| None | 1.0 | 1.0 | 100$^f$ | 76 | 14 | 10 | | | | | | |
| Acetate | 1.0 | 1.0 | 104 | 73 | 15 | 11 | | | | | | |
| Propionate | 0.88 | 0.96 | 28 | 69 | 22 | 8 | | | | | | |
| Butyrate | 0.8 | 0.93 | 49 | 28 | 58 | 15 | | | | | | |
| Hexanoate | 0.75 | 0.83 | 56 | 2 | 2 | — | 67 | 29 | | | | |
| Caprylate | 0.73 | 0.8 | 84 | 17 | 9 | 5 | | | 33 | 36 | | |
| Nonanoate | 0.72 | 0.85 | 95 | — | — | — | | | | | 75 | 25 |
| Caprate | 0.71 | 0.86 | 184 | 17 | 91 | 2 | | | | | | |
| Undecanoate | 0.76 | 0.9 | 136 | 11 | 3 | 26 | | | | | 17 | 16 |
| Undecylenate | 0.71 | 0.87 | 153 | 27 | 56 | 2 | | | | | | |
| Laurate | 0.71 | 0.9 | 154 | 43 | 54 | 3 | | | | | | |
| Tridecanoate$^g$ | 0.7 | 0.76 | 64 | 40 | 19 | 5 | | | | | 12 | 28 |
| Myristate | 0.7 | 0.81 | 207 | 10 | 85 | 5 | | | | | | |
| Oleate | 0.7 | 0.9 | 142 | 49 | 48 | 3 | | | | | | |
| Decyl Alcohol | 0.67 | 0.86 | 157 | 22 | 75 | 3 | | | | | | |

$^a$Respiration Quotient
$^b$Abbreviations as follows: "C$_6$A" = A nucleus with a C$_6$ side chain
$^c$Undecanoate and tridecanoate precursors each produced two additional unknown factors [amounts: 13 and 14% (undecanoate) and 7 and 8% (tridecanoate)]
$^d$For metabolism as sole carbon source
$^e$Represents glucose metabolism or co-metabolism with glucose
$^f$1100 mcg/mL
$^g$In 50% methyl oleate

EXAMPLE 11

Whole fermentation broth from a large tank (4600 L), prepared as described in Example 2, was adjusted to pH 6.5 with HCl and filtered through a filter press with the aid of 4% Celite 545 to give 4600 L of filtrate having a pH of 6.3.

The filtrate was absorbed batch-wise onto Diaion HP-20 resin (200 L), adjusted to pH 6.0 and maintained at this pH while stirring for 2 hours. The mixture was filtered, and the filtrate was discarded.

The saturated HP-20 resin was transferred to a small tank with a welded membrane. The resin was washed first with water (800 L), agitating for 35 minutes, and then with solvent No. 4a (400 L), agitating for 3 minutes. These washes were discarded. The resin was then eluted twice with solvent No. 4 (600 L), agitating for 35 minutes.

The eluates were combined (1200 L) and chromatographed on an IRA-68 resin column (100 L), equilibrated in solvent No. 4 and washed with this solvent (500 L). The column was then eluted with CH$_3$CN:0.2N HOAC (1:1), discarding the first fractions (300 L) and combining, concentrating and lyophilizing subsequent fractions (750 L) to give 3.65 kg of antibiotic A54145.

EXAMPLE 12

Separation of A54145B, A54145C, A54145D and A54145E

Antibiotic A54145 (60 g), obtained as described in Example 4, was subjected to preparative HPLC using a Chromatospac 100, 4-L Quantum LP-1/C18 silica-gel column (3"×39"). The antibiotic was dissolved in solvent No. 1 and added to the column. Elution was monitored by UV at 280 nm.

Fractions were combined based on analytical HPLC as described supra, but detecting at 289 and 223 nm and collecting 500-mL fractions at a flow rate of 100 mL/min. The column was eluted as follows:

| Solvent No. | Fractions |
|---|---|
| 1 | 1–8 |
| 3b | 9–29 |
| 3c | 30–73 |
| 3d | 74–161 |
| 4 | 8-L strip |

On the basis of the analytical HPLC results, fractions 114-161 were combined to give a total of 8.5 g of antibiotic A54145 enriched with components B, C, D and E. This material was rechromatographed on a Chromatospac column, repeating the previous conditions, but detecting at 223 nm and using the following solvents:

| Solvent No. | Fractions |
|---|---|
| 1 | 1–8 |
| 3c | 9–41 |
| 3f | 42–60 |
| 3h | 61–83 |
| 4 | 8-L strip |

From this column, fractions 76–78 gave 1.75 g of A54145B-enriched material, fractions 79–83 gave 1.02 g of A54145C-enriched material and the strip fraction gave 0.8 g of A54145D-enriched material.

EXAMPLE 13

Separation of A54145 Enriched with A54145A, A54145C and A54145F

A54145 (60 g), obtained as described in Example 11, was chromatographed as in Example 12, but using the following solvents:

| Solvent No. | Fractions |
|---|---|
| 1 | 1–8 |
| 3c | 9–102 |
| 4 | 103–122 |

Fractions were combined on the basis of analytical HPLC to give 2.54 g of A54145F-enriched material, 5.1 g of A54145A-enriched material and 10.56 g of A54145C-enriched material.

EXAMPLE 14

Isolation of A54145A

A54145A-enriched material (1 g), obtained as described in Example 13, was purified, using the following preparative HPLC system: two 1"×12" stainless steel columns packed with Zorbax ODS (12μ) in series.
Detection: UV at 280 nm
Flow Rate: 9 mL/minute The material was dissolved in solvent No. 1 for injection onto the column. The column was eluted as follows:

| Solvent No. | Fractions[a] |
| --- | --- |
| 1 | 1–18 |
| 3a | 19–145 |
| 4 | 146–165 |

[a]Fraction volume = 18 mL

Fractions containing A54145A (fractions 86-96) were combined, concentrated under vacuum and lyophilized to give 212 mg of purified A54145A.

EXAMPLE 15

Isolation of A54145B

The A54145B-enriched material obtained in Example 12 (500 mg) was chromatographed using the procedure of Example 14. The column was eluted as follows:

| Solvent No. | Fractions[a] |
| --- | --- |
| 1 | 1–16 |
| 3g | 17–95 |
| 5 | 96–115 |

[a]Fraction volume = 18 mL

Fractions containing A54145B (fractions 64–70) were combined, concentrated under vacuum and lyophilized to give 330 mg of purified A54145B.

EXAMPLE 16

Isolation of A54145C

A54145C-enriched material (11.76 g), obtained as described in Examples 12 and 13, was purified using the following preparative HPLC system:
Column: 2"×60-cm stainless steel
Packing: Quantum LP-1/C18 silica gel (20 mμ)
Detection: UV at 280 nm
Flow Rate: 18 mL/min The material was dissolved in pyridine/HOAc/H₂O (1:1:98, 37 mL) for application to the column. The column was eluted as follows:

| Solvent No. | Fractions[a] |
| --- | --- |
| 1 | 1–10 |
| 3e | 11–160 |
| 3h | 161–550 |
| 4 | 551–582 |

[a]Fraction volume = 18 mL

Fractions containing A54145C were combined (fractions 320–331, 817.8 mg). This material (800 mg) was further purified by HPLC using a 1"×20" stainless-steel column packed with Quantum LP-1/C18 (20 mμ) silica-gel column, detecting as in Example 10, and applying the material in pyridine/HOAc/H₂O (1:1:98, 15 mL). The column was eluted at a flow rate of 8 mL/min as follows:

| Solvent No. | Fractions[a] |
| --- | --- |
| 1 | 1–18 |
| 3f | 19–69 |
| 3g | 70–114 |
| 5 | 115–137 |

[a]Fraction volume = 16 mL

Fractions containing A54145C (fractions 84–86 and 92–98) were combined, concentrated and lyophilized to give 350 mg of C-enriched material.

This process was repeated with some variation in the solvents used, i.e., varying the amount of CH₃CN in the solvent and sometimes eliminating methanol in the solvent mixture, to give 27.6 mg of purified A54145C.

EXAMPLE 17

Isolation of A54145D

A54145D-enriched material (750 mg), obtained as described in Example 12, was purified using the preparative HPLC system described in Example 14, except that only one column was used. The material was applied to the column in 25 mL of the solvent, and the column was eluted at a flow rate of 7.5 mL/min as follows:

| Solvent No. | Fractions[a] |
| --- | --- |
| 1 | 1–6 |
| 3g | 7–89 |
| 2k | 90–101 |
| 4 | 102–115 |

[a]Fraction volume = 15 mL

Fractions containing A54145D (19–22) were combined, concentrated and lyophilized to give 219 mg of material further enriched with A54145D.

This material was purified by a second HPLC column, using the same conditions except that 5% methanol was added to solvent 4 and solvent 2k was eliminated.

The fractions from this column containing A54145D (fractions 72–74) were combined, concentrated and lyophilized to give 70 mg of purified A54145D.

EXAMPLE 18

Isolation of A54145E

A54145E-enriched material (1.0 g), obtained as described in Example 12, was purified using a preparative HPLC system as in Example 16, but using a 1"×20" column. The material was applied in 15 mL of solvent, and the column was eluted at a flow rate of 9 mL/min as follows:

| Solvent No. | Fractions[a] |
| --- | --- |
| 1 | 1–19 |
| 2h | 20–118 |
| 2j | 119–215 |

-continued

| Solvent No. | Fractions[a] |
|---|---|
| 4 | 216–225 |

[a]Fraction volume = 18 mL

Fractions containing A54145E (fractions 147–160) were combined, concentrated and lyophilized to give 49.7 mg of material further enriched with A54145E.

This material was purified using two 9.4- x 250-mm Zorbax ODS (5μ) columns in series, detecting by UV at 280. The material was applied to the column in 3 mL of solvent 1, and the column was eluted at a flow rate of 3.25 mL/min as follows:

| Solvent No. | Fractions[a] |
|---|---|
| 1 | 1–12 |
| 2i | 13–180 |
| 4 | 181–193 |

[a]Fraction volume = 6.5 mL

Fractions containing A54145E (fractions 143–160) were combined, concentrated and lyophilized to give 16.07 mg of purified A54145E.

EXAMPLE 19

Isolation of A54145F

A54145F-enriched material (800 mg), obtained as described in Example 13, was purified using an HPLC system as in Example 16 but with a 1"×20" column. The material was applied to the column in 10 mL of solvent 1, and the column was eluted at a flow rate of 8 mL/min as follows:

| Solvent No. | Fractions[a] |
|---|---|
| 1 | 1–10 |
| 2f | 11–60 |
| 2g | 61–99 |
| 2k | 100–134 |
| 4 | 135–150 |

[a]Fraction volume = 16 mL

Fractions containing A54145F (fractions 120–128) were combined, concentrated and lyophilized to give 366.2 mg of purified A54145F.

EXAMPLE 20

Isolating A54145$_1$

A54145A$_1$-enriched material was obtained using the following procedure: Whole broth (103 L), prepared as described in Example 1, was treated as described in Example 4 except that instead of the IRA-68(OAc$^-$) column, the combined eluates were chromatographed over a 40-×780-mm BioRex 5 (Cl$^-$) column, using gradient elution with a 0.1N - 1.0N NaCl solvent system and collecting 100-mL fractions.

Fractions containing A54145 were combined and desalted over a 40-×400-mm HP-20 column, again collecting 100-mL fractions. Fractions containing A54145 were combined and lyophilized to give 12.08 g of antibiotic A54145.

A portion of this antibiotic A54145 (2 g) is subjected to preparative HPLC using a Waters PrepPak 500 (C18) column, using a linear gradient of from water to H$_2$O:CH$_3$CN(1:1) containing 1% NH$_4$H$_2$PO$_4$. Fractions containing A54145A$_1$ are collected and desalted over an HP-20 column, eluting with Solvent 4.

This step is repeated twice, and the A$_1$-enriched material is combined (937 mg).

The A$_1$-enriched material is chromatographed over two 1"×12" Zorbax ODS columns in series as described in Example 10. Fractions containing A54145A$_1$ are eluted with Solvent 2j, combined, concentrated and lyophilized to give crude A54145A$_1$ (109 mg).

This material is further purified by repeating this step to give more purified A54145A$_1$ (69.29 mg).

The material is even further purified by repeating this procedure three times, using Solvents 3j, 3h and 3k, respectively. The product obtained is desalted over HP-20 to give purified A54145A$_1$ (12.21 mg).

EXAMPLE 21

Alternate Isolation of A54145B

Whole fermentation broth (100 L), prepared as described in Example 3, was worked up as described in Example 4 except that chromatography on IRA-68 was omitted. The material was eluted from HP-20 with solvent 4a, concentrated and freeze-dried to give 248.2 g of crude antibiotic A54145.

A portion of this material (60 g) was chromatographed on a 2"×60-cm LP-1/C18 silica gel column.

Detection: UV at 254 and 280 mm.
Flow Rate: 25 mL/minute/fraction.
The column was eluted as follows:

| Solvent No. | Fractions |
|---|---|
| 1 | 1–138 |
| 2f | 139–411 |
| 2h | 412–560 |
| 2m | 561–976 |
| 4 | 977–1000 |

Fractions containing A54145B and A54145B$_1$ were pooled and concentrated as follows:

| Pool | Fraction | Weight(g) |
|---|---|---|
| 1 | 951–1000 | 1.10 |
| 2 | 635–667 | 4.62 |
| 3 | 685–719 | 3.95 |

The A54145B-enriched fraction (Pool 1) was further purified over two 1"×12" Amicon C18 columns in series.

Detection: UV at 280 mm.
Flow Rate: 20 mL/1.6 minute/fraction.
The column was eluted with pyridine/HOAc/H$_2$O/CH$_3$CN (0.1/0.1/67.3/32.5). A54145B-enriched fractions (#93–130) were combined and concentrated to give 394.5 mg of A54145B.

EXAMPLE 22

Isolating A54145B$_1$

The A54145B and A54145B$_1$-enriched fractions obtained in Example 21 (Pools 2 and 3) were also further purified by HPLC over two 1"×12" Amicon C18 columns as in Example 2. Fractions containing A54145B were combined to give an additional 544 mg of A54145B.

Fractions containing A54145B$_1$ were combined to give 207 mg of purified A54145B$_1$.

EXAMPLE 23

Alternate Isolation of A54145A$_1$

Whole fermentation broth (160 L) is prepared as described in Example 9. With this procedure, the fermentation volume increases with time; therefore, beginning at 138 hours, 10-L aliquots are removed at intervals and frozen. By harvest (287 hours), a total of 50 L is removed and frozen. The frozen broth is added back to the fermentation at harvest. The whole broth is filtered with a filter aid or separated using a centrifuge. A portion of the filtrate (55 L) is worked up using the procedure of Example 21. Fractions containing A54145A$_1$ are eluted with solvent 4, concentrated and freeze-dried. Following this procedure gave 111.3 g of A54145A$_1$-enriched material.

This material is chromagraphed over a 1"×16" Zorbax C8 (12μ) column. The column is eluted with solvent 2h. Following this procedure gave 374 mg of further A54145A$_1$-enriched material, which contained approximately 46% A54145A$_1$, 19% A54145B$_1$, 14% A54145A, A54145B and 8% of an unidentified material (HPLC analysis).

Preparative HPLC using appropriate solvents is carried out on the further purified material to obtain A54145A$_1$ in pure form.

EXAMPLE 24

A54145-Improved Broiler Starter Ration

The following recipe provides a balanced broiler starter ration adapted to feed chicks for improved weight gains.

| Ingredient | Percent | Lbs/Ton |
|---|---|---|
| Ground Yellow Corn | 55.99 | 1119.8 |
| Animal - Vegetable Fat | 3.13 | 62.6 |
| Soybean Meal (48%) | 32.37 | 647.4 |
| Fish Meal | 2.50 | 50.0 |
| Feather Meal - Hydr. | 2.50 | 50.0 |
| Dicalcium Phosphate | 1.66 | 33.2 |
| Ground Limestone | 0.77 | 15.4 |
| Salt | 0.30 | 6.0 |
| Vitamin Premix[1] | 0.50 | 10.0 |
| Trace Mineral Premix[2] | 0.10 | 2.0 |
| Methionine Hyd. Anal. | 0.13 | 2.6 |
| A54145 Premix[3] | 0.05 | 1.0 |
| Total | 100.00 | 2000.0 |

[1]Vitamin premix provides 3000 IU of vitamin A, 900 ICU of vitamin D$_3$, 40 mg of vitamin E, 0.7 mg of vitamin K, 1000 mg of choline, 70 mg of niacin, 4 mg of pantothenic acid, 4 mg of riboflavin, 100 mcg of vitamin B$_{12}$, 100 mcg of biotin and 125 mg of ethoxyquin per kg of complete feed.
[2]Trace mineral premix provides 75 mg of manganese, 50 mg of zinc, 25 mg of iron, 1 mg of iodine and 0.1 mg of selenium per kg of complete feed.
[3]Premix containing 1-20 g of antibiotic A54145 per pound premix provides a corresponding 1-20 g of A54145/ton of finished feed.

This diet is usually fed to chicks from day 1 until a day between 17 and 28.

EXAMPLE 25

A54145-Improved Broiler Finisher Ration

The following recipe provides a balanced broiler finisher ration adapted to feed chicks for improved weight gains:

| Ingredient | Percent | Lbs/Ton |
|---|---|---|
| Ground Yellow Corn | 66.35 | 1327.0 |
| Animal - Vegetable Fat | 1.53 | 30.6 |
| Corn Glut. Meal (60%) | 4.00 | 80.0 |
| Soybean Meal (48%) | 19.19 | 383.8 |
| Fish Meal | 2.50 | 50.0 |
| Feather Meal - Hydr. | 2.50 | 50.0 |
| Dicalcium Phosphate | 1.71 | 34.2 |
| Ground Limestone | 0.83 | 16.6 |
| Salt | 0.30 | 6.0 |
| Vitamin Premix[1] | 0.50 | 10.0 |
| Trace Mineral Premix[2] | 0.10 | 2.0 |
| Methionine Hyd. Anal. | 0.15 | 3.0 |
| Lysine HCl | 0.29 | 5.8 |
| A54145 Premix[3] | 0.05 | 1.0 |
| Total | 100.00 | 2000.0 |

[1]Vitamin premix provides 3000 IU of vitamin A, 900 ICU of vitamin D$_3$, 40 mg of vitamin E, 0.7 mg of vitamin K, 1000 mg of choline, 70 mg of niacin, 4 mg of pantothenic acid, 4 mg of riboflavin, 100 mcg of vitamin B$_{12}$, 100 mcg of biotin and 125 mg of ethoxyquin per kg of complete feed.
[2]Trace mineral premix provides 75 mg of manganese, 50 mg of zinc, 25 mg of iron, 1 mg of iodine and 0.1 mg of selenium per kg of complete feed.
[3]Premix containing 1-20 g of antibiotic A54145 per pound premix provides a corresponding 1-20 g of A54145/ton of finished feed.

This diet is fed to chicks aged from about 17 to about 28 days old until either withdrawal or sacrifice.

We claim:

1. A54145A, which has the following characteristics:
   Mol. Wt.: 1643
   Mol. Formula: $C_{72}H_{109}N_{17}O_{27}$
   High Resolution FABMS(M+H): Found: 1644.7778, Calcd. for $C_{72}H_{110}N_{17}O_{27}$: 1644.7757
   UV (EtOH) $\lambda_{max}$: 219 nm ($\epsilon$ 35,000), 280 ($\epsilon$ 5,250), shoulder 288 ($\epsilon$ 4,600)
   Optical Rotation: $[\alpha]_{589}^{25°}$ C. No Rotation (CH$_3$OH); $[\alpha]_{365}^{25°}$ C. $-14.0°$ (c 1.0, CH$_3$OH)
   Amino-acid Analysis: Asp 973(2), Thr 441(1), Glu 1056(2), Gly 528(1), Ala 549(1), Ile 469(1), Trp 465(1)
   $^1$H NMR (360 MHz): FIG. 1;
   or a pharmaceutically acceptable salt of A54145A.

2. A54145B, which has the following characteristics:
   Mol. Wt.: 1657
   Mol. Formula: $C_{73}H_{111}N_{17}O_{27}$;
   High Resolution FABMS(M+H): Found: 1658.7954, Calcd. for $C_{73}H_{112}N_{17}O_{27}$: 1658.7914
   UV (EtOH) $\lambda_{max}$: 220 nm ($\epsilon$ 41,854), 281 ($\epsilon$ 5,613), 289 ($\epsilon$ 5,084)
   IR (KBr): FIG. 9;
   Optical Rotation: $[\alpha]_{589}^{25°}$ C. $= -8.55°$ (c 0.47, H$_2$O); $[\alpha]_{365}^{25°}$ C. $= -36.32°$ (c 0.47, H$_2$O)
   Amino-acid Analysis: Asp 1039(2), Thr 466(1), Glu 564(1), Gly 528(1), Ala 525(1), Ile 491(1), Lys 514(1), Trp 491(1), 3-Me-Glu 512(1).
   $^1$H NMR (360 MHz): FIG. 2;
   or a pharmaceutically acceptable salt of A54145B.

3. A54145C, which has the following characteristics:
   Mol. Wt.: 1657
   Mol. Formula: $C_{73}H_{111}N_{17}O_{27}$
   High Resolution FABMS(M+H): Found: 1658.7905, Calcd. for $C_{73}H_{112}N_{17}O_{27}$: 1658.7914
   UV (EtOH) $\lambda_{max}$: 219 nm ($\epsilon$ 29,500), 281 ($\epsilon$ 4,200), 288 ($\epsilon$ 3,600)
   Amino-acid Analysis: Asp 934(2), Thr 414(1), Glu 594(1), Gly 501(1), Ala 459(1), Val 359(1), Lys 451(1), 3-MG 487(1), Trp 308(1).
   $^1$H NMR (360 MHz): FIG. 3;
   or a pharmaceutically acceptable salt of A54145C.

4. A54145D, which has the following characteristics:
   Mol. Wt.: 1657
   Mol. Formula: $C_{73}H_{111}N_{17}O_{27}$;

High Resolution FABMS(M+H): Found: 1658.7913, Calcd. for $C_{73}H_{112}N_{17}O_{27}$: 1658.7914

UV (EtOH) $\lambda_{max}$: 219 nm ($\epsilon$ 37,500), 280 ($\epsilon$ 5,200), 288 ($\epsilon$ 4,500)

Amino-acid Analysis: Asp 1011(2), Thr 427(1), Glu 967(2), Gly 515(1), Ala 487(1), Ile 434(1), Lys 543(1), Trp 577(1)

$^1$H NMR (270 MHz): FIG. 4;

or a pharmaceutically acceptable salt of A54145D.

5. A54145E, which has the following characteristics:
Mol. Wt.: 1671
Mol. Formula: $C_{74}H_{113}N_{17}O_{27}$
High Resolution FABMS(M+H): Found: 1672.8065, Calcd. for $C_{74}H_{114}N_{17}O_{27}$: 1672.8069

UV (EtOH) $\lambda_{max}$: 221 nm ($\epsilon$ 29,714), 278 ($\epsilon$ 4,577), 289 (4,044)

Amino-acid Analysis: Asp 826(2), Thr 367(1), Glu 494(1), Gly 437(1), Ala 422(1), Ile 378(1), Lys 410(1), Trp 387(1), 3-MG 437(1)

$^1$H NMR (270 MHz): FIG. 5;

or a pharmaceutically acceptable salt of A54145E.

6. A54145F, which has the following characteristics:
Mol. Wt.: 1629
Mol. Formula: $C_{71}H_{107}N_{17}O_{27}$
High Resolution FABMS(M+H): Found: 1630.7634, Calcd. for $C_{71}H_{108}N_{17}O_{27}$: 1630.7601

UV (EtOH) $\lambda_{max}$: 219 nm ($\epsilon$ 36,750), 280 ($\epsilon$ 5,100), 288 ($\epsilon$ 4,450)

Optical Rotation: $[\alpha]_{589}^{25°} = -3.0°$ (c 1.0, $H_2O$); $[\alpha]_{365}^{25°\ C.} = -6.0°$ (c 1.0, $H_2O$)

Amino-acid Analysis: Asp 959(2), Thr 428(1), Glu 965(2), Gly 494(1), Ala 487(1), Val 363(1), Lys 492(1), Trp 452(1).

$^1$H NMR (270 MHz): FIG. 6;

or a pharmaceutically acceptable salt of A54145F.

7. A54145A, which has the following characteristics:
Mol. Wt.: 1643
Mol. Formula: $C_{72}H_{109}N_{17}O_{27}$
High Resolution FABMS(M+H): Found: 1644.7691, Calcd. for $C_{72}H_{110}N_{17}O_{27}$: 1644.7757

UV (EtOH) $\lambda_{max}$: 220 nm ($\epsilon$ 41,623), 281 ($\epsilon$ 5,750), 289 ($\epsilon$ 4,950)

Optical Rotation: $[\alpha]_{589}^{25°\ C.} - 10.4°$ (c 0.69, $CH_3OH$)

Amino-acid analysis: Asp 1209(2), Thr 554(1), Glu 1209(2), Gly 636(1), Ala 617(1), Ile 576(1), Lys 604(1), Trp 514(1)

$^1$H NMR (500 MHz): FIG. 7;

or a pharmaceutically acceptable salt of A54145$A_1$.

8. A54145$B_1$, which has the following characteristics:
Mol. Wt.: 1657
Mol. Formula: $C_{73}H_{111}N_{17}O_{27}$
High Resolution FABMS(M+H): Found: 1658.7911, Calcd. for $C_{73}H_{112}N_{17}O_{27}$: 1658.7914

UV (EtOH) $\lambda_{max}$: 221 nm (e 39,100), 282 ($\epsilon$, 5,500), 290 ($\epsilon$ 4,740)

Figure 8:
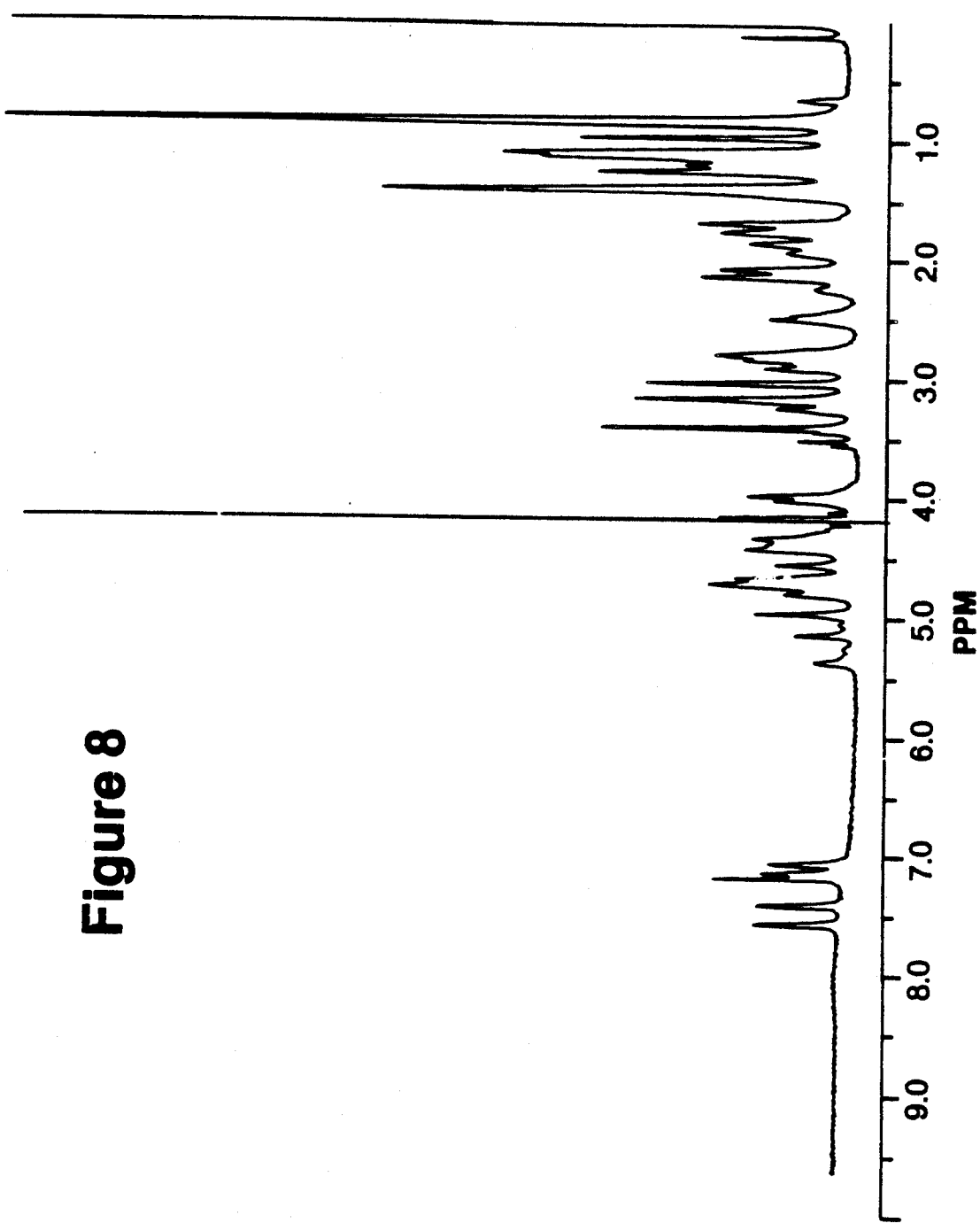

Amino-acid Analysis: Asp 935(2), Thr 422(1), Glu 556(1), Gly 480(1), Ala 434(1), Ile 438(1), Lys 467(1), Trp 440(1), 3-MG 426(1);

$^1$H 10 :H NMR (500 MHz): FIG. 8 or a pharmaceutically acceptable salt of A54145$B_1$.

9. Antibiotic A54145 comprising A54145A and A54145$B_1$, which is produced by submerged aerobic fermentation of a *Streptomyces fradiae* strain selected from NRRL 18158, NRRL 18159 and NRRL 18160 or an A54145-producing mutant thereof.

10. A feed composition for improving growth performance in animals comprising animal feed and an effective amount of antibiotic A54145 of claim 9.

11. A feed composition for improving growth performance in animals comprising animal feed and an effective amount of a compound of claim 1.

12. A feed composition for improving growth performance in animals comprising animal feed and an effective amount of a compound of claim 2.

13. A feed composition for improving growth performance in animals comprising animal feed and an effective amount of a compound of claim 8.

14. A feed composition of claim 10 wherein the animals are poultry.

15. A feed composition of claim 11 wherein the animals are poultry.

16. A feed composition of claim 12 wherein the animals are poultry.

17. A feed composition of claim 13 wherein the animals are poultry.

18. A method for improving growth performance in an animal which comprises administering to the animal an effective amount of antibiotic A54145 of claim 9.

19. A method for improving growth performance in an animal which comprises administering to the animal an effective amount of a compound of claim 1.

20. A method for improving growth performance in an animal which comprises administering to the animal an effective amount of a compound of claim 2.

21. A method for improving growth performance in an animal which comprises administering to the animal an effective amount of a compound of claim 8.

22. A method of claim 18 wherein the animal is a fowl.

23. A method of claim 19 wherein the animal is a fowl.

24. A method of claim 20 wherein the animal is a fowl.

25. A method of claim 21 wherein the animal is a fowl.

* * * * *

UNITED STATES PATENT AND TRADEMARK OFFICE
CERTIFICATE OF CORRECTION

PATENT NO. : 4,994,270

DATED : February 19, 1991

INVENTOR(S) : LaVerne D. Boeck, et al

It is certified that error appears in the above-indentified patent and that said Letters Patent is hereby corrected as shown below:

Column 34:
Claim 1, lines 31-32, "Optical Rotation: $[\alpha]_{589}^{25°C}$. No Rotation (CH$_3$OH); $[\alpha]_{365}^{25°C}$. -14.0° (c 1.0, CH$_3$OH)" should read --Optical Rotation: $[\alpha]_{589}^{25°C}$ No Rotation (CH$_3$OH)

$[\alpha]_{365}^{25°C}$ -14.0° ($\underline{c}$ 1.0, CH$_3$OH)--

Column 34
Claim 2, lines 46-47, "Optical Rotation: $[\alpha]_{589}^{25°C}$. = -8.55° (c 0.47, H$_2$O); $[\alpha]_{365}^{25°C}$. = -36.32° (c 0.47, H$_2$O)" should read --Optical Rotation: $[\alpha]_{589}^{25°C}$ = -8.55° ($\underline{c}$ 0.47, H$_2$O)

$[\alpha]_{365}^{25°C}$ = -36.32° ($\underline{c}$ 0.47, H$_2$O)--

Column 35
Claim 6, lines 31-32, "Optical Rotation: $[\alpha]_{589}^{25°}$ = -3.0° ($\underline{c}$ 1.0, H$_2$O); $[\alpha]_{365}^{25°}$ C. = -6.0° (c 1.0, H$_2$O)" should read --Optical Rotation: $[\alpha]_{589}^{25°C}$ = -3.0° ($\underline{c}$ 1.0, H$_2$O)

$[\alpha]_{365}^{25°C}$ = -6.0° ($\underline{c}$ 1.0, H$_2$O)--

UNITED STATES PATENT AND TRADEMARK OFFICE
CERTIFICATE OF CORRECTION

PATENT NO. : 4,994,270

DATED : February 19, 1991

INVENTOR(S) : LaVerne D. Boeck, et al

It is certified that error appears in the above-indentified patent and that said Letters Patent is hereby corrected as shown below:

Column 35
Claim 7, line 39, "A54145A, which has the following characteristics:" should read --$A54145A_1$, which has the following characteristics:--

Claim 7, line 46, "Optical Rotation: $[\alpha]589^{25°C}$. - 10.4° (c 0.69, $CH_3OH$)", should read --Optical Rotation: $[\alpha]_{589}^{25°C}$ -10.4° ($\underline{c}$ 0.69, $CH_3OH$)--

Signed and Sealed this

Eighth Day of February, 1994

Attest:

BRUCE LEHMAN

Attesting Officer

Commissioner of Patents and Trademarks